US010939889B2

(12) United States Patent
Flexman et al.

(10) Patent No.: US 10,939,889 B2
(45) Date of Patent: Mar. 9, 2021

(54) OPTICAL SHAPE SENSING FOR FLUOROSCOPIC SURGICAL NAVIGATION

(71) Applicant: KONINKLIJKE PHILIPS N.V., Eindhoven (NL)

(72) Inventors: Molly Lara Flexman, Melrose, MA (US); David Paul Noonan, New York, NY (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 296 days.

(21) Appl. No.: 15/736,124

(22) PCT Filed: Jun. 16, 2016

(86) PCT No.: PCT/IB2016/053557
§ 371 (c)(1),
(2) Date: Dec. 13, 2017

(87) PCT Pub. No.: WO2017/001959
PCT Pub. Date: Jan. 5, 2017

(65) Prior Publication Data
US 2018/0153498 A1    Jun. 7, 2018

Related U.S. Application Data

(60) Provisional application No. 62/186,874, filed on Jun. 30, 2015.

(51) Int. Cl.
*A61B 6/00* (2006.01)
*A61B 34/20* (2016.01)
(Continued)

(52) U.S. Cl.
CPC ............ *A61B 6/547* (2013.01); *A61B 6/12* (2013.01); *A61B 6/4441* (2013.01); *A61B 34/20* (2016.02);
(Continued)

(58) Field of Classification Search
CPC ......... A61B 6/547; A61B 34/20; A61B 90/37; A61B 6/4441; A61B 6/12; A61B 2090/376; A61B 2034/2061
See application file for complete search history.

(56) References Cited

U.S. PATENT DOCUMENTS 9,625,254 B2    4/2017 Manzke
9,675,304 B2    6/2017 Jain
(Continued)

FOREIGN PATENT DOCUMENTS

WO    2014009853 A2    1/2014
WO    WO-2014009853 A2 *    1/2014    ........... A61B 5/6833
WO    WO-2014009853 A3 *    3/2014    ........... A61B 5/1135

*Primary Examiner* — Amelie R Davis
*Assistant Examiner* — Adil Partap S Virk

(57) ABSTRACT

A fluoroscopic surgical system employing a FORS sensor (40), a navigation controller (70), a fluoroscopic imager (30) and a mechanical connector (50) adjoined to the fluoroscopic imager (30). In operation, mechanical connector (50) is utilized to detachably attach FORS senor to fluoroscopic imager (30), whereby navigation controller (70) processes a shape reconstruction of FORS sensor (40) relative to a reference point fixed or movable within an operating space (20) for controlling a tracking of fluoroscopic imager (30) within the operating space (20). The system may further employ a surgical instrument (60) whereby, concurrently or subsequently to a fluoroscopic imaging of a patient anatomy, FORS sensor (40) is thereafter detached from fluoroscopic imager (30) and detachably attached to surgical instrument (60), or FORS sensor (40) is concurrently detachably attached to fluoroscopic imager (30) and surgical instrument (60). The navigation controller (70) processes an additional shape reconstruction of FORS sensor (40) relative to the reference point within the operating space (20) for controlling a tracking of surgical instrument (60) within the operating space (20).

20 Claims, 19 Drawing Sheets

(51) Int. Cl.
   *A61B 90/00*      (2016.01)
   *A61B 6/12*       (2006.01)
(52) U.S. Cl.
   CPC ...... *A61B 90/37* (2016.02); *A61B 2034/2061* (2016.02); *A61B 2090/376* (2016.02)

(56) References Cited

U.S. PATENT DOCUMENTS

| | | |
|---|---|---|
| 9,757,034 B2 | 9/2017 | Desjardins et al. |
| 10,028,791 B2 | 7/2018 | Prisco |
| 2004/0097805 A1 | 5/2004 | Verard |
| 2009/0137952 A1* | 5/2009 | Ramamurthy ........... A61B 5/06 604/95.01 |
| 2010/0030063 A1 | 2/2010 | Lee |
| 2013/0150732 A1 | 6/2013 | Manzke |
| 2013/0188855 A1* | 7/2013 | Desjardins ............. A61B 90/98 382/131 |
| 2013/0308137 A1* | 11/2013 | Manzke ................ G01B 11/18 356/511 |
| 2013/0310685 A1* | 11/2013 | Chan ...................... G01B 11/18 600/424 |
| 2013/0317356 A1* | 11/2013 | Ramachandran ...... A61B 5/064 600/424 |
| 2014/0088413 A1* | 3/2014 | Von Bucsh .......... A61B 5/0084 600/424 |
| 2015/0190205 A1* | 7/2015 | Grass ..................... G01L 1/246 600/408 |
| 2016/0015293 A1 | 1/2016 | Denissen |

* cited by examiner

OPTICAL SHAPE SENSING FOR FLUOROSCOPIC SURGICAL NAVIGATION

CROSS-REFERENCE TO PRIOR APPLICATIONS

This application is the U.S. National Phase application under 35 U.S.C. § 371 of International Application Serial No. PCT/IB2016/053557, filed on Jun. 16, 2016, which claims the benefit of U.S. Patent Application No. 62/186,874, filed on Jun. 30, 2015. This application is hereby incorporated by reference herein.

FIELD OF THE INVENTION

The present disclosure generally relates to tracking a fluoroscopic imager and a surgical tool during any type of fluoroscopic based surgical procedure (e.g., spinal surgery, trauma surgery, oncology and neurosurgery). The present disclosure specifically relates to a novel and inventive incorporation of a Fiber-Optical RealShape ("FORS") sensor for tracking a fluoroscopic imager and a surgical tool during any type of fluoroscopic based surgical procedure.

BACKGROUND OF THE INVENTION

One orthopedic instrument known in the art is a Kirschner wire ("k-wire") as a guide, anchor, or for stabilizing bone fragments. More particularly, a k-wire is a metal wire having a small diameter (e.g., 1-5 mm) and is drilled into bone on a temporary or permanent basis. A k-wire may be utilized alone or with cannulated screws for stabilizing fractures or for fixation of the spine. K-wires are also used in the fixation of fractures and in trauma surgery.

Another orthopedic instrument known in the art is a Jamshidi® needle ("j-needle"), which is a cylindrical needle having a tapered cutting tip insertable within a lumen of the needle. A key feature of the j-needle is the flat handle surface that can be used with a mallet to tap and insert the needle into bone. After insertion into the bone and upon removal of the cutting tip from within the lumen, a k-wire or other tool is inserted within the lumen of the needle.

An exemplary pedicle screw placement as known in the art generally consists of:
(1) positioning a patient prone on a table;
(2) positioning a C-arm to acquire a good view of the patient's pedicle;
(3) creating access to the patient's spine;
(4) docking a j-needle on the junction between the transverse process and the facet complex;
(5) gently tapping the j-needle with a mallet to advance the j-needle through the pedicle, either freehand or under fluoroscopic visualization;
(6) upon the j-needle reaching one quarter or half the depth of the vertebral body, removing the cutting tip from the lumen of the j-needle and inserting a k-wire into the lumen of the j-needle;
(7) passing the k-wire further into the bone and removing the j-needle;
(8) placing cannulated muscle dilators over the k-wire; and
(9) tapping the pedicle and placing the appropriate cannulated screw.

In the above spinal fusion, it is important to accurately place screws within the pedicle in order to fuse two or more vertebrae of the spine, particularly due to the close proximity of vital nerves and vessels. For freehand placement of a pedicle screw as described above, there are high rates of misplacement and critical breaches. Image-guided surgery for orthopedics is therefore preferred.

Specifically, imaging is used in spinal surgery for both pre-operative planning and assessment and for intra-operative guidance (e.g., CT, MM, Fluoroscopy, X-ray, etc.). Intraoperative fluoroscopy is commonly used to verify the positioning of the j-needle and/or k-wire before the drill or screw is placed in position. The drawback of fluoroscopy is that it imparts ionizing radiation to both the patient and the doctor, and it provides a two-dimensional ("2D") projection of a three-dimensional ("3D") position. Thus, clinicians will frequently attempt to gain a 3D perspective at minimal radiation exposure to the patent and doctor by obtaining orthogonal 2D fluoroscopy views, most common being anteroposterior and lateral views as known in the art. To obtain such views using a single detector C-arm, it is necessary to rotate the arm through ninety degrees (90°). This presents workflow challenges in the operating room. In addition, only one view from the single detector C-arm is available at any point in time.

Computer assisted surgery involves the addition of a navigation tool to pre-operative and/or intra-operative imaging in order to provide 3D guidance of tools with respect to the anatomy during the procedure. In some orthopedic procedures (e.g., spinal fusion and pedicle screw placement), there are typically pre-operative CT images or intra-operative 3D x-ray images that can be used to create a bi-plane view during navigation as known in the art. When using such 3D images, live tool information in terms of a position and orientation of the tool is not available in the image without some tool tracking and registration. Most commonly optical tracking is used to track the tool position relative to the patient anatomy. This requires optical trackers to be attached to the working instruments and those trackers must always remain in the camera line-of-sight. The advantage of optical tracking is that a single camera can be used with multiple trackers at the same time. Therefore multiple working instruments can be tracked as well as the position of the c-arm. However, one significant disadvantage of optical tracking is the optical trackers must always remain in the camera line-of-sight. Another disadvantage of optical tracking is the optical trackers are quite large and thus must be attached at the proximal end of any orthopedic instrument. This limits an ability of optical trackers to track small and flexible orthopedic instruments which lack the sufficient stiffness to infer tip position from a proximally attached optical tracker (e.g., a k-wire).

More particular to orthopedic procedures, intra-operative fluoroscopic images are used for navigation and these images are derived from a mobile c-arm that can be positioned in and around the patient when needed, and moved away from the patient at other times. The mobile C-arm is not equipped to provide real-time information in terms of a position and an orientation of the mobile C-arm in the operating room, and therefore the mobile C-arm needs to be tracked relative to the patient and instruments to allow for navigation.

SUMMARY OF THE INVENTION

The present disclosure provides inventions utilizing a Fiber-Optical RealShape ("FORS") sensor for tracking a fluoroscopic imager and a surgical instrument within an operating space during a surgical procedure.

For purposes of the inventions of the present disclosure, the term "Fiber-Optical RealShape ("FORS") sensor"

broadly encompasses an optical fiber structurally configured as known in the art for extracting high density strain measurements of the optical fiber derived from light emitted into and propagated through the optical fiber and reflected back within the optical fiber in an opposite direction of the propagated light and/or transmitted from the optical fiber in a direction of the propagated light.

An example of a FORS sensor includes, but is not limited to, an optical fiber structurally configured under the principle of Optical Frequency Domain Reflectometry (OFDR) for extracting high density strain measurements of the optical fiber derived from light emitted into and propagated through the optical fiber and reflected back within the optical fiber in an opposite direction of the propagated light and/or transmitted from the optical fiber in a direction of the propagated light via controlled grating patterns within the optical fiber (e.g., Fiber Bragg Gratings), a characteristic backscatter of the optical fiber (e.g., Rayleigh backscatter) or any other arrangement of reflective element(s) and/or transmissive element(s) embedded, etched, imprinted, or otherwise formed in the optical fiber.

Commercially and academically, Fiber-Optical RealShape may also be known as optical shape sensing ("OSS").

For purposes of the inventions of the present disclosure, the terms "surgical procedure", "fluoroscopic imager" and "surgical instrument" are to be interpreted as understood in the art of the present disclosure and as exemplary described herein.

Examples of general categories of a surgical procedure include, but are not limited to, cardiovascular, gynecology, abdominal, neurosurgery, obstetrics, ophthalmology, orthopedic, otolaryngology, reconstructive, thoracic, and urology. More particularly, examples of orthopedic procedures include, but are not limited to, spinal surgery, joint/knee/hip/shoulder/ankle replacements, rotary cuff repair, ACL reconstruction, trauma, and arthroscopic surgery.

Examples of a fluoroscopic imager include, but is not limited to, a fixed C-arm and a mobile C-arm for real-time X-ray imaging of a patient anatomy.

Examples of a surgical instrument in the form of surgical tools include, but are not limited to, scalpels, cauterizers, ablation devices, needles, forceps, k-wires and associated drivers, endoscopes, awls, screwdrivers, osteotomes, chisels, mallets, curettes, clamps, forceps, periosteomes and j-needles.

Examples of surgical instruments in the form of implantable implements include, but are not limited to, needles, pins, nails, screws, and plates.

For purposes of the inventions of the present disclosure, the term "tracking" and any tenses thereof are to be interpreted as understood in the art of the present disclosure and as exemplary described herein.

For purposes of the inventions of the present disclosure, the term "operating space" broadly encompasses any area of a room whereby a surgical procedure is being performed, particularly as related to a patient anatomy.

One form of the inventions of the present disclosure is a fluoroscopic surgical system employing a FORS sensor, a navigation controller, a fluoroscopic imager and a mechanical connector adjoined to the fluoroscopic imager. In operation, the mechanical connector is utilized to detachably attach the FORS senor to the fluoroscopic imager, whereby the navigation controller processes sensing data informative of a shape reconstruction of the FORS sensor relative to a reference point fixed or movable within an operating space for controlling a tracking of the fluoroscopic imager within the operating space.

A second form of the inventions of the present disclosure is the fluoroscopic surgical system further employing a surgical instrument whereby, concurrently or subsequently to a fluoroscopic imaging of a patient anatomy by the imager, the FORS sensor is thereafter detached from the fluoroscopic imager and detachably attached to the surgical instrument, or the FORS sensor is concurrently detachably attached to the fluoroscopic imager and the surgical instrument. The navigation controller processes sensing data informative of an additional shape reconstruction of the FORS sensor relative to the reference point fixed or movable within the operating space for controlling a tracking of the surgical instrument within the operating space.

Alternatively, the FORS sensor may serve as the surgical instrument whereby, concurrently or subsequently to a fluoroscopic imaging of a patient anatomy by the imager, the FORS sensor remains detachably attached to the fluoroscopic imager or is detached from the fluoroscopic imager. The navigation controller processes sensing data informative of an additional shape reconstruction of the FORS sensor relative to the reference point fixed or movable within the operating space for controlling a tracking of the FORS sensor serving as a surgical instrument within the operating space.

For purposes of the inventions of the present disclosure, the term "mechanical connector" broadly encompasses any connector of the art structurally configured for detachably attaching the FORS sensor to the fluoroscopic imager whereby the fluoroscopic imager and the FORS sensor maintain distinct and separate mechanical operation while in synchronized motion.

For purposes of the inventions of the present disclosure, the term "adjoin" and any tense thereof broadly encompassing any type of permanent or detachable coupling, connecting, affixing, clamping, mounting, etc. of components involving direct physical contact between the components or an adjacent placement of the components, and the term "detachably attach" and tenses thereof broadly encompasses a detachable adjoining of components involving direct physical contact between the components or an adjacent placement of the components.

For purposes of the inventions of the present disclosure, the terms "sensing data" and "shape reconstruction" are to be interpreted as understood in the art of the present disclosure and as exemplary described herein.

For purposes of the present disclosure, the term "controller" broadly encompasses all structural configurations of an application specific main board or an application specific integrated circuit housed within or linked to a workstation for controlling an application of various inventive principles of the present invention as subsequently described herein. The structural configuration of the controller may include, but is not limited to, processor(s), computer-usable/computer readable storage medium(s), an operating system, application module(s), peripheral device controller(s), slot(s) and port(s).

For purposes of the present disclosure, the label "navigation" used herein for the term "controller" distinguishes for identification purposes the navigation controller from other controllers as described and claimed herein without specifying or implying any additional limitation to the term "controller".

Examples of a "workstation" include, but are not limited to, an assembly of one or more computing devices, a display/monitor, and one or more input devices (e.g., a keyboard, joysticks and mouse) in the form of a client computer, a desktop or a tablet.

For purposes of the present disclosure, the term "application module" broadly encompasses a component of the workstation consisting of an electronic circuit and/or an executable program (e.g., executable software and/firmware) for executing a specific application.

A third form of the inventions of the present disclosure is a fluoroscopic surgical method involving (1) a FORS sensor detachably attached to a fluoroscopic imager, (2) the FORS sensor, based on the mechanical attachment of the FORS sensor to the fluoroscopic imager, generating sensing data informative of a shape reconstruction of the FORS sensor relative to a reference position fixed or movable within an operating space, (3) a navigation controller controlling a tracking of the fluoroscopic imager within the operating space responsive to the sensing data generated by the FORS sensor based on the mechanical attachment of the FORS sensor to the fluoroscopic imager, (4a) the FORS sensor being detached from the fluoroscopic imager and detachably attached to a surgical instrument, or the FORS sensor being concurrently detachably attached to the fluoroscopic imager and the surgical instrument, (5a) the FORS sensor, based on the mechanical attachment of the FORS sensor to the surgical instrument, generating sensing data informative of the shape reconstruction of the FORS sensor relative to a fixed reference position within an operating space, and (6a) the navigation controller controlling a tracking of the surgical instrument within the operating space responsive to the sensing data generated by the FORS sensor based on the mechanical attachment of the FORS sensor to the surgical instrument.

Alternatively in view of an omission of a surgical instrument as known in the art, the method involves (4b) the FORS sensor detached from the fluoroscopic imager and serving as a surgical instrument, or the FORS sensor remaining detachably attached to the fluoroscopic imager and serving as the surgical instrument, (5b) the FORS sensor, based on the FORS sensor serving as the surgical instrument, generating sensing data informative of the shape reconstruction of the FORS sensor relative to a reference fixed or movable position within an operating space, and (6b) the navigation controller controlling a tracking of the FORS sensor within the operating space responsive to the sensing data generated by the FORS sensor based on the FORS sensor serving as the surgical instrument.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

DETAILED DESCRIPTION OF THE PREFERRED EMBODIMENTS

The inventions of the present disclosure proposes a FORS sensing solution that that facilitates a registration between a fluoroscopic imager/surgical instrument(s) and an intraoperative imaging of a patient anatomy preferably using a single FORS sensor. The registration is achievable by alternatively attaching the FORS sensor to the fluoroscopic imager during an image acquisition phase whereby the acquired fluoroscopic image is registered within an operating space (e.g., a patient coordinate frame) and to the surgical instrument(s) during an instrument navigation phase whereby a position and an orientation of the surgical instrument is known within the operating space.

Figure 1:
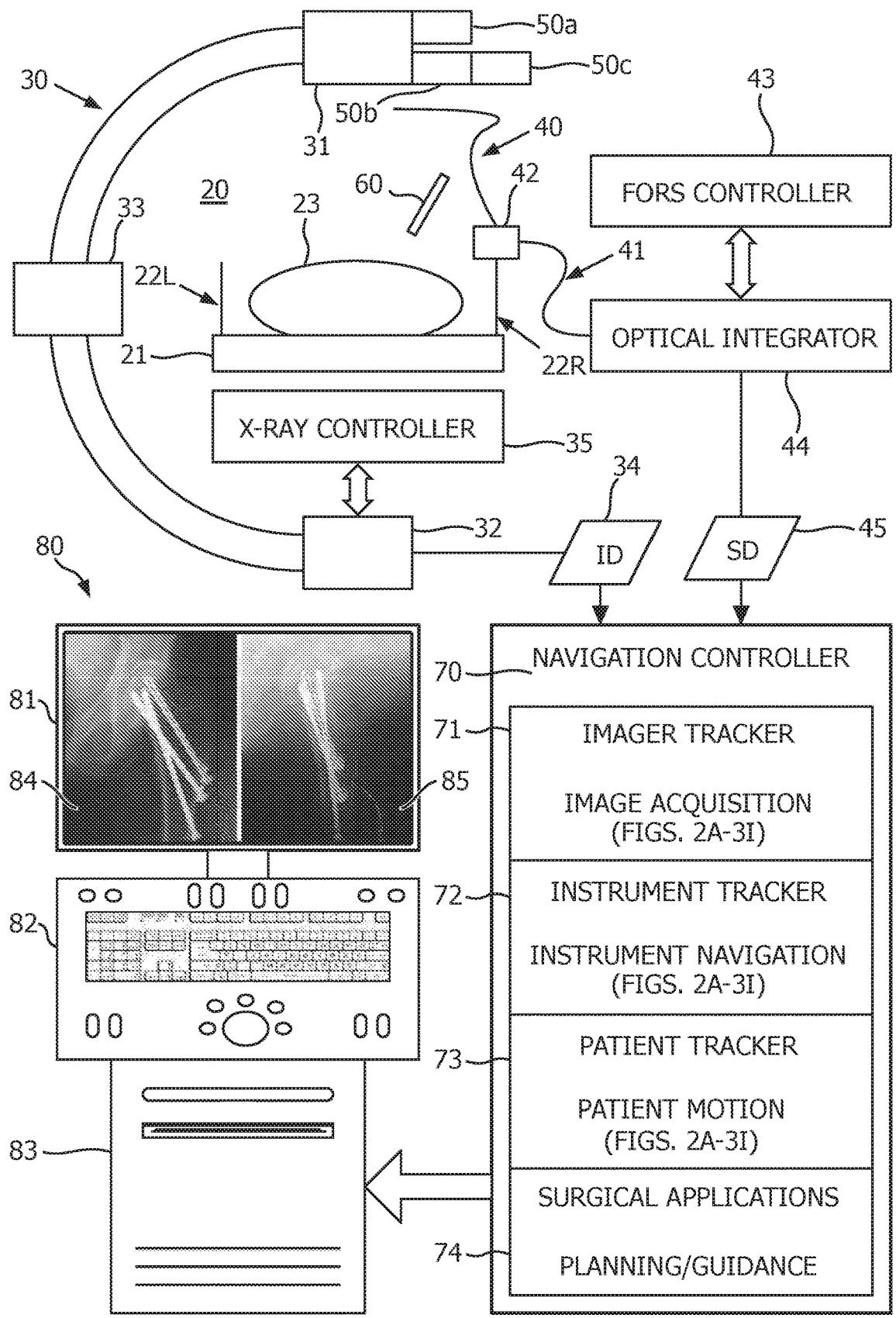
FIG. 1 illustrates an exemplary fluoroscopic surgical system, particularly for bi-plane imaging, in accordance with the inventive principles of the present invention.

To facilitate an understanding of the various inventions of the present disclosure, the following description of FIG. 1 teaches basic inventive principles of an implementation of a FORS sensing by a fluoroscopic surgical system during a surgical procedure. From this description, those having ordinary skill in the art will appreciate how to apply the inventive principles of the present disclosure for making and using additional embodiments of fluoroscopic surgical systems and methods of the present disclosure. Please note the components of the present disclosure as shown in FIG. 1 are not drawn to scale, but drawn to conceptually visualize the inventive principles of the present disclosure.

Referring to FIG. 1, a fluoroscopic surgical system of the present disclosure employs a fluoroscopic imager 30 (e.g., a mobile c-arm as shown), a FORS sensor 40, a mechanical connector 50, a surgical instrument 60 of any type, and a navigation controller 70 for executing a surgical procedure involving a patient 23 lying prone on an operating table 21 within an operating space 20.

As known in the art, fluoroscopic imager 30 generally includes an X-ray generator 31, an image intensifier 32 and a collar 33 for rotating fluoroscopic imager 30. In operation, fluoroscopic imager 30 generates imaging data 34 illustrative of a fluoroscopic image of an anatomical area of patient 23.

FORS sensor 40 includes an optical fiber having controlled grating patterns (e.g., Fiber Bragg Gratings), a characteristic backscatter (e.g., Rayleigh backscatter) or any other arrangement of reflective elements and/or transmissive elements embedded, etched, imprinted, or otherwise formed in the optical fiber. In practice, the controlled gratings, characteristic backscatter, or reflective/transmissive elements may extend along any portion and an entirety of the optical fiber. Also in practice, FORS sensor 40 may include of one or more or individual fibers that may or may not be helixed.

In practice, the optical fiber of FORS sensor 40 may be made partially or entirely of any glass, silica, phosphate glass or other glasses, or made of glass and plastic or plastic, or other materials used for making optical fibers. For impeding any damage to FORs sensor 40 when introduced into the patient anatomy via manual or robotic insertion, the optical fiber of FORS sensor 40 is embedded into a medical device (e.g., a guide wire or a catheter) or permanently encircled by a protective sleeve. In practice, the protective sleeve may be made from any flexible material of a specified hardness including, but not limited to, pebax, nitinol, furcation tubing, and stranded metal tubing. Also in practice, protective sleeve may consist of two or more tubular components of same or different degrees of flexibility and hardness in an overlapping and/or sequential arrangement.

In operation, FORS sensor 40 is distally extends from launch 42 adjoined to a rail 22R of operating table 21 and an optical fiber 41 proximally extends from launch 42 to an optical integrator 44. In practice, optical fiber 41 may be a separate optical fiber connected to FORS sensor 40 at launch 42, or a proximal extension of FORS sensor 40.

As known in the art, a FORS controller 43 controls an emission of light by optical integrator 44 via optical fiber 41 into FORS sensor 40 whereby the light is propagated through FORS sensor 40 to the distal end thereof to generate sensing data 45 informative of shape reconstruction of FORS sensor 40 relative to launch 42 serving as a fixed reference position within operating space 20. In practice, the distal end of FORS sensor 40 may be closed, particularly for light reflective embodiments of FORS sensor 40, or may be opened, particularly for light transmissive embodiments of FORS sensor 40.

Mechanical connector 50 is adjoined to fluoroscopic imager 31 at X-ray generator 31 as shown or any other suitable location, and is used to detachably attach FOR sensor 40 to fluoroscopic imager 30 as will be further described in the present disclosure. In one embodiment, mechanical connector 50 is a single piece connector 50a. In an alternative embodiment, mechanical connector 50 is a multi-piece connector including a connector base 50b and a connector clip 50c.

In operation, mechanical connector 50 alternatively attaches FORS sensor 40 to fluoroscopic imager 30 during an image acquisition phase whereby the acquired fluoroscopic imaging data 34 is registered within operating space 20 (e.g., a patient coordinate frame) and to surgical instrument 60 during an instrument navigation phase whereby a position and an orientation of surgical instrument 60 is known within the operating space.

Navigation controller 70 is installed within a workstation 80 including a known arrangement of a monitor 81, a keyboard 81 and a computer 83.

Navigation controller 70 includes application modules in the form of an image tracker 71, an instrument tracker 72, a patient tracker 73 and surgical applications 74.

With FORS sensor 40 being attached to fluoroscopic imager 30 via mechanical connector 30, image tracker 71 tracks a position and orientation of fluoroscopic imager 33 within operating space 20 derived from a shape reconstruction of FORS sensor 40 as known in the art based on a calibration of mechanical connector 50a or connector base 50b to fluoroscopic imager 30 as known in the art With FORS sensor 40 being attached to fluoroscopic imager 30 via mechanical connector 50, image tracker 71 tracks a position and orientation of fluoroscopic imager 30 within operating space 20 derived from a shape reconstruction of FORS sensor 40 as known in the art based on a calibration of mechanical connector 50a or connector base 50b to fluoroscopic imager 30 as known in the art.

In practice, surgical instrument 60 may be omitted whereby FORS sensor 40 additionally serves as a surgical instrument including, but not limited to, FORS sensor 40 serving as a guide wire. For such embodiments, instrument tracker 72 tracks a position and orientation of FORS sensor 40 serving as the surgical instrument within operating space 20 derived from a shape reconstruction of FORS sensor 40 as known in the art.

With FORS sensor 40 being attached to patient 73 by any viable means, patient tracker 73 tracks a motion of patient 23 within operating space 20 derived from a shape reconstruction of FORS sensor 40 as known in the art based on a calibration of FORS sensor to patient anatomy 23 as known in the art.

Surgical applications 74 includes one or more known applications for performing the surgical procedure including, but not limited to, an image planning application for plaining trajectories and positioning of surgical instrument 50 and tools attached thereto within patient 23, and an image guidance application for displaying an overlay of surgical instrument 60 onto the fluoroscopic image and/or operative images (e.g., bi-plane X-ray images 84 and 85 as shown displayed by monitor 81). Examples of the operative images include, but are not limited to, pre-operative and/or intra-operative CT, MRI or X-ray images.

Still referring to FIG. 1, to further facilitate an understanding of the various inventions of the present disclosure, the following description of FIGS. 2A-2F teaches basic inventive principles of an implementation of FORS sensing by a fluoroscopic surgical system during a surgical procedure incorporating a mechanical connector 50a (FIG. 1). From this description, those having ordinary skill in the art will appreciate how to apply the inventive principles of the present disclosure for making and using additional embodiment of fluoroscopic surgical systems and methods of the present disclosure incorporating mechanical connector 50a. Please note the components of the present disclosure as shown in FIGS. 2A-2F are not drawn to scale, but drawn to conceptually visualize the inventive principles of the present disclosure.

Figure 2A:
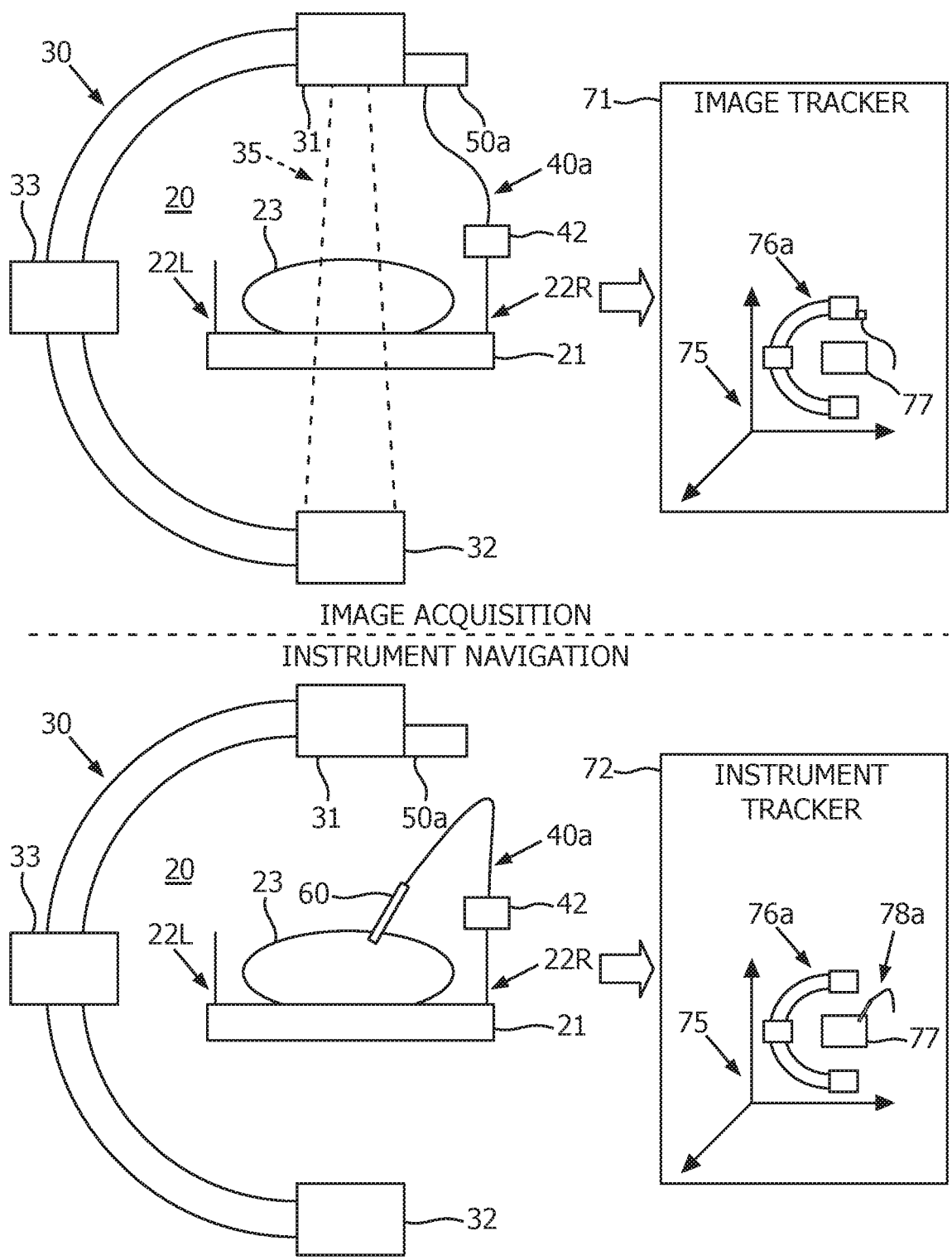
FIGS. 2A-2F illustrates six (6) exemplary embodiments of the fluoroscopic surgical navigation of FIG. 1 employing an integrated mechanical connector having in accordance with the inventive principles of the present disclosure.

Referring to FIG. 2A, an image acquisition phase of the illustrated surgical procedure involves a detachable attachment of FORS sensor 40a to fluoroscopic imager 30 via an embedding of FORS sensor 40a into mechanical connector 50a. Prior to, concurrently or subsequently, the image acquisition phase further involves an emission of X-rays 35 by fluoroscopic imager 30. Image tracker 71 tracks a position and an orientation of resulting fluoroscopic image 77 within a coordinate system 75 of operating space 20 (e.g., a patient coordinate system) derived from a shape reconstruction 76a of FORS sensor 40a as attached to fluoroscopic imager 30.

A following instrument navigation phase of the surgical procedure involves a detachment of FORS sensor 40a from fluoroscopic imager 30 and an embedding of FORS sensor 40a into surgical instrument 60. Instrument tracker 72 tracks a position and an orientation of surgical instrument 60 within coordinate system 75 of operating space 20 derived from a shape reconstruction 78a of FORS sensor 40a as attached to surgical instrument 60.

Figure 2B:
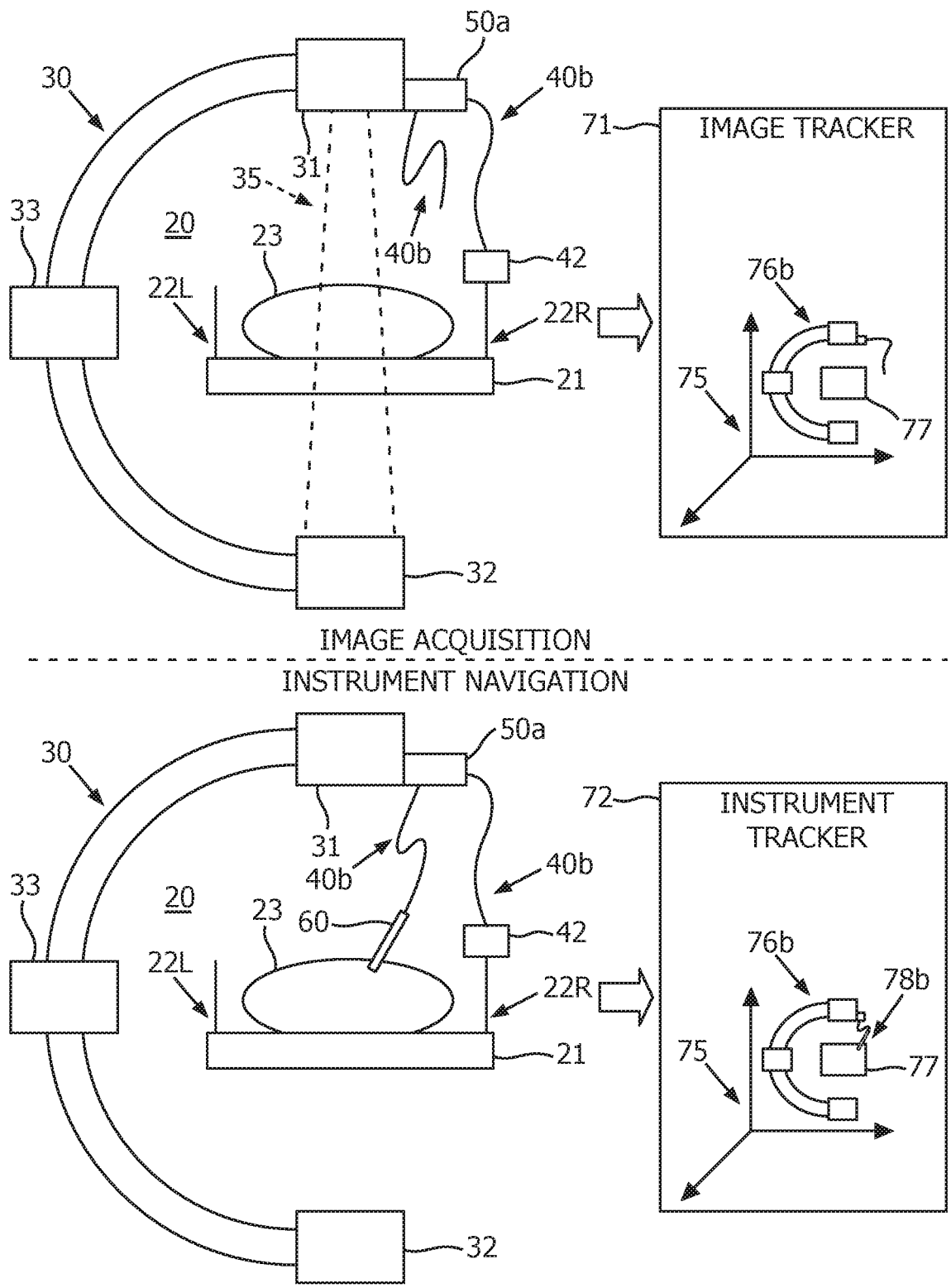

Referring to FIG. 2B, an image acquisition phase of the illustrated surgical procedure involves a detachable attachment of FORS sensor 40b to fluoroscopic imager 30 via an embedding of FORS sensor 40b through mechanical connector 50a. Prior to, concurrently or subsequently, the image acquisition phase further involves an emission of X-rays 35 by fluoroscopic imager 30. Image tracker 71 tracks a position and an orientation of resulting fluoroscopic image 77 within a coordinate system 75 of operating space 20 (e.g., a patient coordinate system) derived from a shape reconstruction 76b of FORS sensor 40b as attached to fluoroscopic imager 30.

FORS sensor 40b is a longer version of FORS sensor 40a (FIG. 2B). As such, the following instrument navigation phase of the surgical procedure involves an embedding of FORS sensor 40b into surgical instrument 60 while maintaining the attachment of FORS sensor 40b to fluoroscopic imager 30 via mechanical connector 50a. Instrument tracker 72 tracks a position and an orientation of surgical instrument 60 within coordinate system 75 of operating space 20 derived from a shape reconstruction 78b of FORS sensor 40b as attached to surgical instrument 60.

Figure 2C:
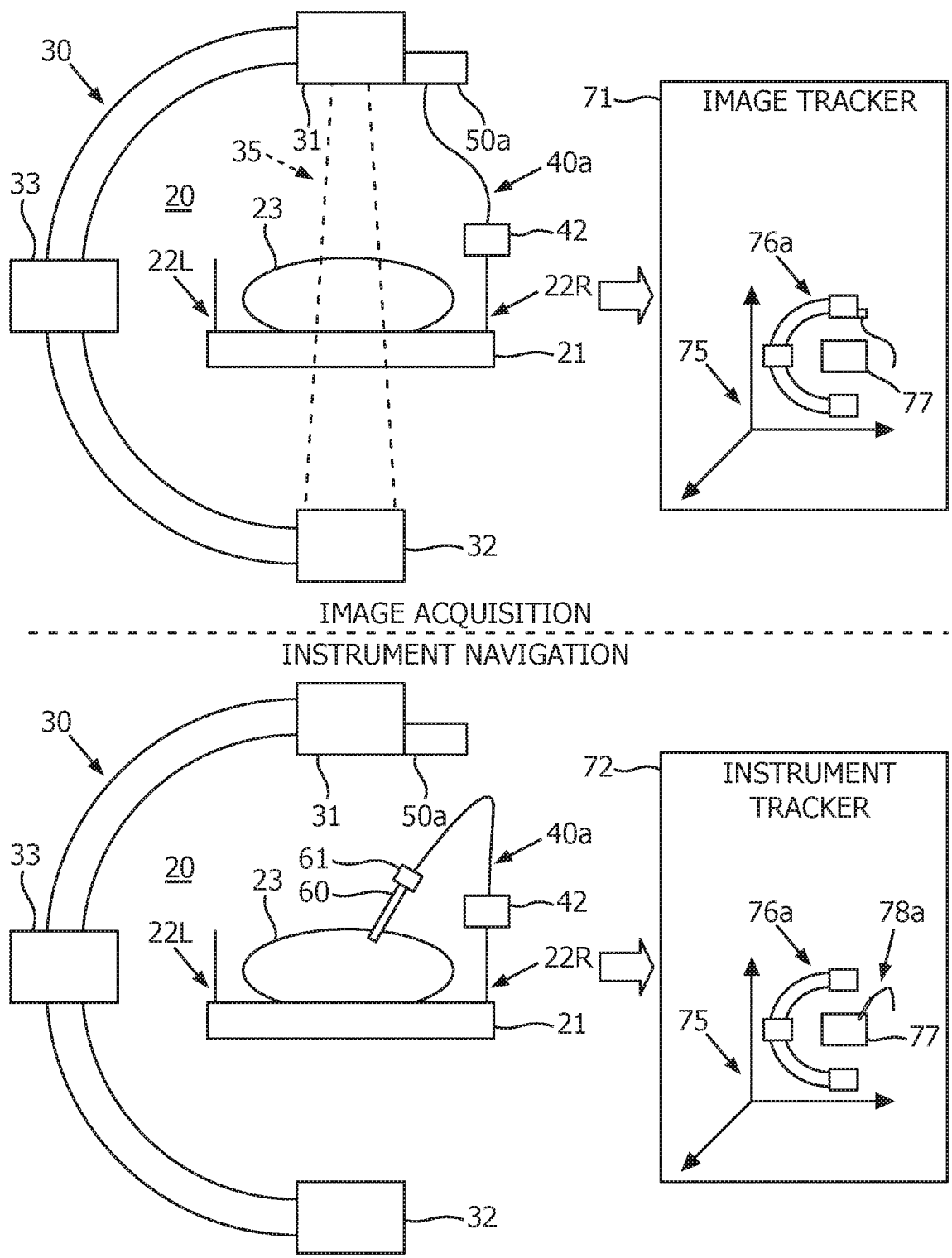

Referring to FIG. 2C, an image acquisition phase of the illustrated surgical procedure involves a detachable attachment of FORS sensor 40a to fluoroscopic imager 30 via an embedding of FORS sensor 40b into mechanical connector 50a. Prior to, concurrently or subsequently, the image acquisition phase further involves an emission of X-rays 35 by fluoroscopic imager 30. Image tracker 71 tracks a position and an orientation of resulting fluoroscopic image 77 within a coordinate system 75 of operating space 20 (e.g., a patient coordinate system) derived from a shape reconstruction 76a of FORS sensor 40a as attached to fluoroscopic imager 30.

In practice, surgical instrument 60 may not be constructed with a lumen or does not have an additional lumen available for FORS sensor 40 of the present disclosure. As such, an instrument connector 61 having a lumen for FORS sensor 50 may be integrated into surgical instrument 60 (e.g., instrument connector 60 may be manufactured as a component of surgical instrument 60 or permanently affixed to surgical instrument 60), or retrofitted onto surgical instrument 60 (e.g., via a detachable press fit or magnetic clamping onto a suitable component of surgical instrument 60).

Based on instrument connector 61, the following instrument navigation phase of the surgical procedure involves a detachment of FORS sensor 40a from fluoroscopic imager 30 and an embedding of FORS sensor 40a into instrument connector 61 clipped, clamped or otherwise connected onto surgical instrument 60. Instrument tracker 72 tracks a position and an orientation of surgical instrument 60 within coordinate system 75 of operating space 20 derived from a shape reconstruction 78a of FORS sensor 40a as attached to surgical instrument 60.

Figure 2D:
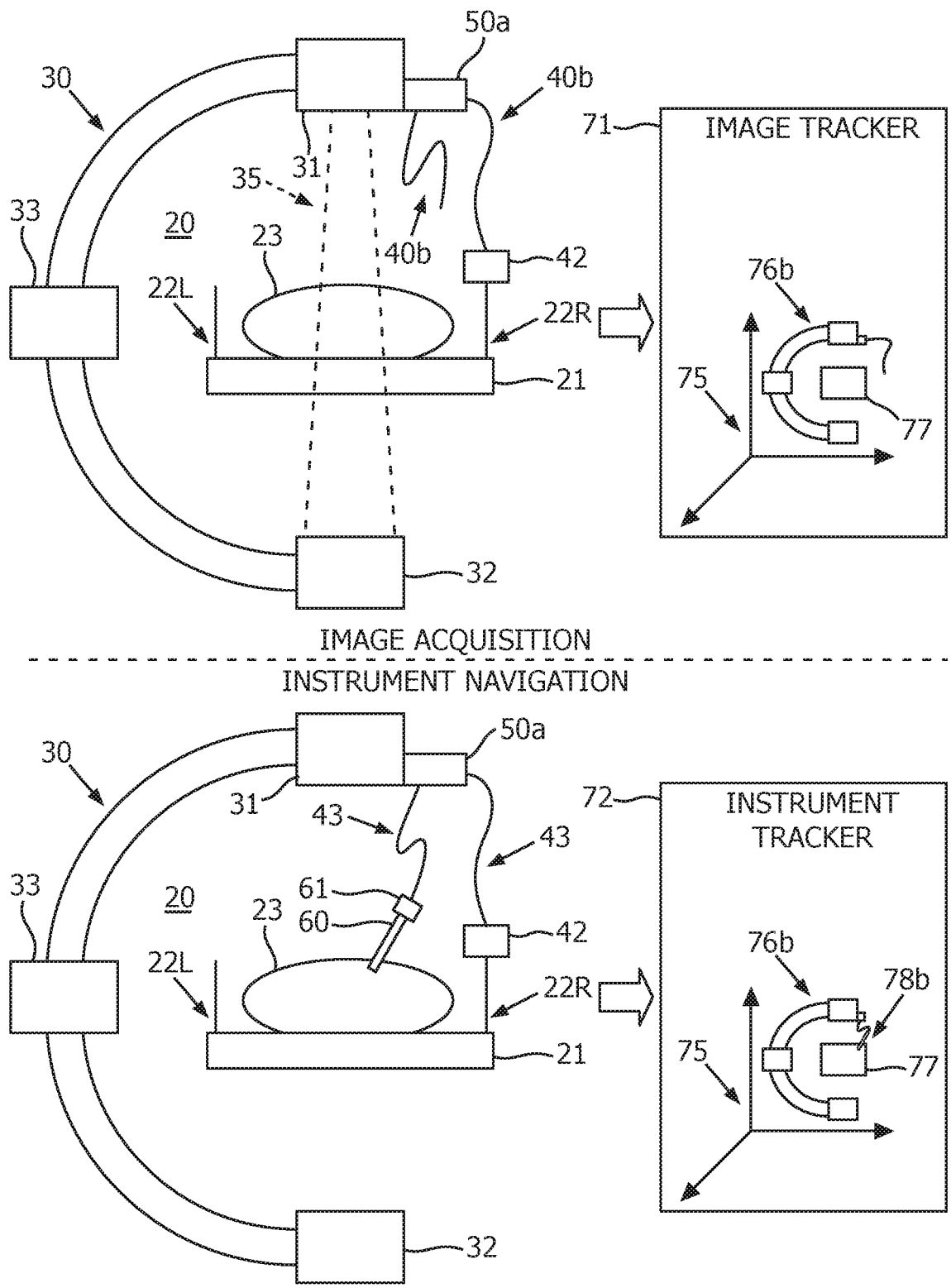

Referring to FIG. 2D, an image acquisition phase of the illustrated surgical procedure involves a detachable attachment of FORS sensor 40b to fluoroscopic imager 30 via an embedding of FORS sensor 40b through mechanical connector 50a. Prior to, concurrently or subsequently, the image acquisition phase further involves an emission of X-rays 35 by fluoroscopic imager 30. Image tracker 71 tracks a position and an orientation of resulting fluoroscopic image 77 within a coordinate system 75 of operating space 20 (e.g., a patient coordinate system) derived from a shape reconstruction 76b of FORS sensor 40b as attached to fluoroscopic imager 30.

The following instrument navigation phase of the surgical procedure involves an embedding of FORS sensor 40b into an instrument connector 61 clipped, clamped or otherwise connected onto surgical instrument 60 while maintaining the attachment of FORS sensor 40b to fluoroscopic imager 30 via mechanical connector 50a. Instrument tracker 72 tracks a position and an orientation of surgical instrument 60 within coordinate system 75 of operating space 20 derived from a shape reconstruction 78b of FORS sensor 40b as attached to surgical instrument 60.

Figure 2E:
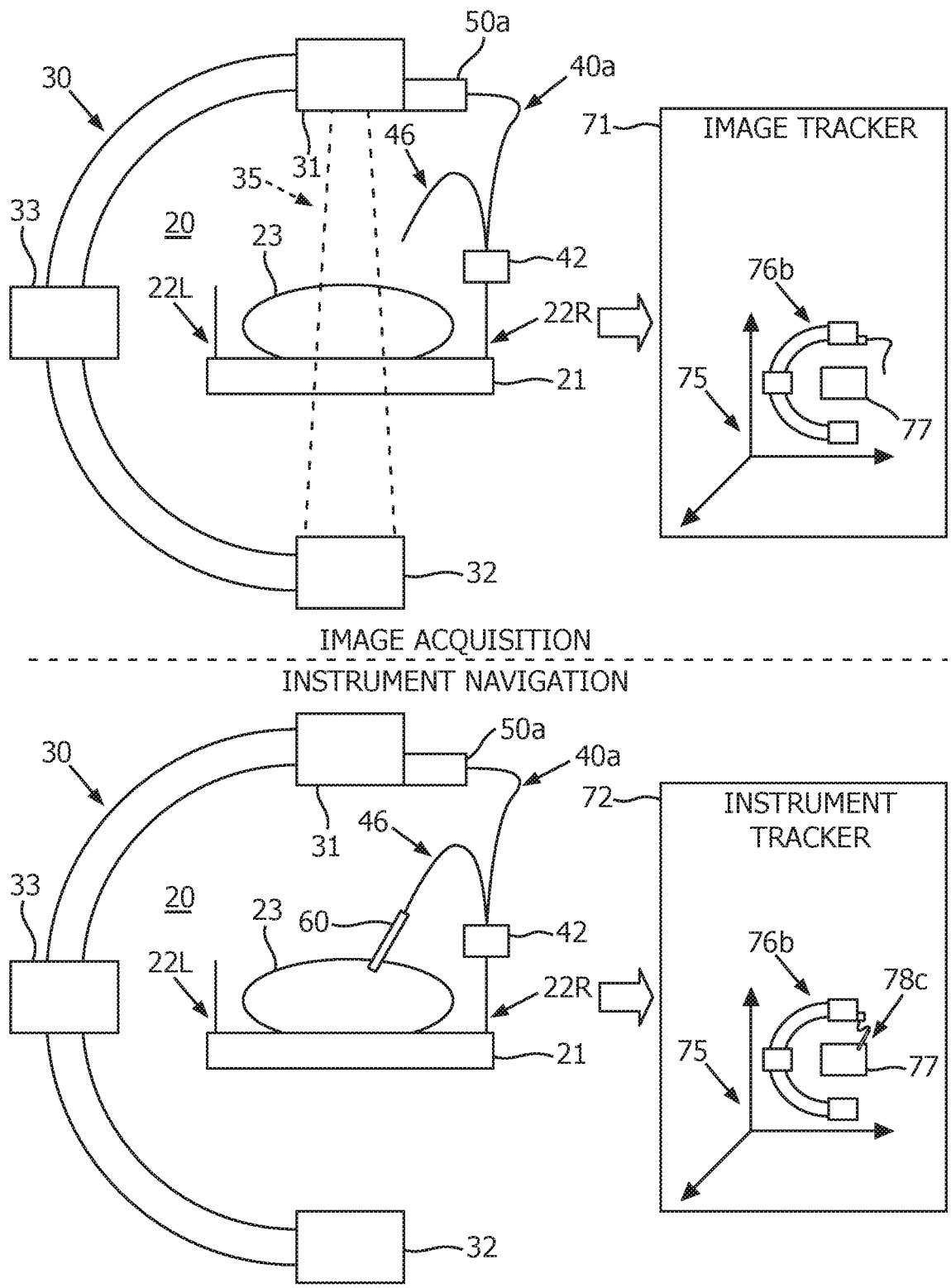

Referring to FIG. 2E, an image acquisition phase of the illustrated surgical procedure involves a detachable attachment of FORS sensor 40a to fluoroscopic imager 30 via an embedding of FORS sensor 40b into mechanical connector 50a. Prior to, concurrently or subsequently, the image acquisition phase further involves an emission of X-rays 35 by fluoroscopic imager 30. Image tracker 71 tracks a position and an orientation of resulting fluoroscopic image 77 within a coordinate system 75 of operating space 20 (e.g., a patient coordinate system) derived from a shape reconstruction 76a of FORS sensor 40a as attached to fluoroscopic imager 30.

A following instrument navigation phase of the surgical procedure involves a an embedding of an auxiliary FORS sensor 46 into surgical instrument 60 while maintaining the attachment of FORS sensor 40a to fluoroscopic imager 30 via mechanical connector 50a. Instrument tracker 72 tracks a position and an orientation of surgical instrument 60 within coordinate system 75 of operating space 20 derived from a shape reconstruction 78c of auxiliary FORS sensor 46 as attached to surgical instrument 60.

Figure 2F:
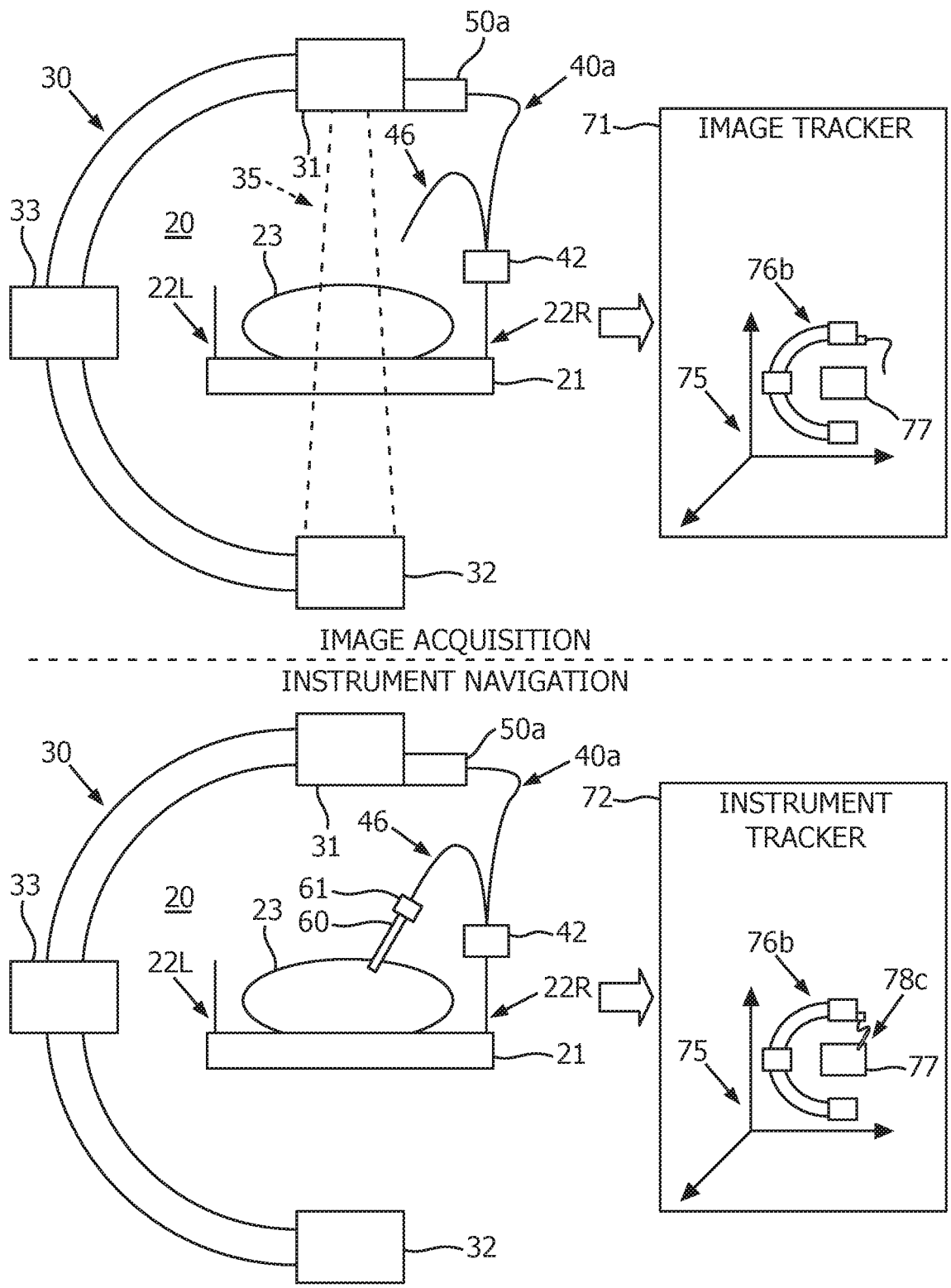

Referring to FIG. 2F, an image acquisition phase of the illustrated surgical procedure involves a detachable attachment of FORS sensor 40a to fluoroscopic imager 30 via an embedding of FORS sensor 40b into mechanical connector 50a. Prior to, concurrently or subsequently, the image acquisition phase further involves an emission of X-rays 35 by fluoroscopic imager 30. Image tracker 71 tracks a position and an orientation of resulting fluoroscopic image 77 within a coordinate system 75 of operating space 20 (e.g., a patient coordinate system) derived from a shape reconstruction 76a of FORS sensor 40a as attached to fluoroscopic imager 30.

A following instrument navigation phase of the surgical procedure involves a an embedding of an auxiliary FORS sensor 46 into an instrument connector 61 clipped, clamped or otherwise connected onto surgical instrument 60 while maintaining the attachment of FORS sensor 40a to fluoroscopic imager 30 via mechanical connector 50a. Instrument tracker 72 tracks a position and an orientation of surgical instrument 60 within coordinate system 75 of operating space 20 derived from a shape reconstruction 78c of auxiliary FORS sensor 46 as attached to surgical instrument 60.

Referring back to FIG. 1, to further facilitate an understanding of the various inventions of the present disclosure, the following description of FIGS. 3A-3I teaches basic inventive principles of an implementation of a FORS sensing by a fluoroscopic surgical system during a surgical procedure incorporating a mechanical connector including a connector base 50b (FIG. 1) and connector clip 50c (FIG. 1). From this description, those having ordinary skill in the art will appreciate how to apply the inventive principles of the present disclosure for making and using additional embodiment of fluoroscopic surgical systems and methods of the present disclosure incorporating a connector base 50b and connector clip 50c. Please note the components of the present disclosure as shown in FIGS. 3A-3I are not drawn to scale, but drawn to conceptually visualize the inventive principles of the present disclosure.

Referring to FIGS. 3A-3I, connector base 50b is adjoined to fluoroscopic imager 30, and connector clip 50c is detachably attachable to connector base 50b.

Figure 3A:
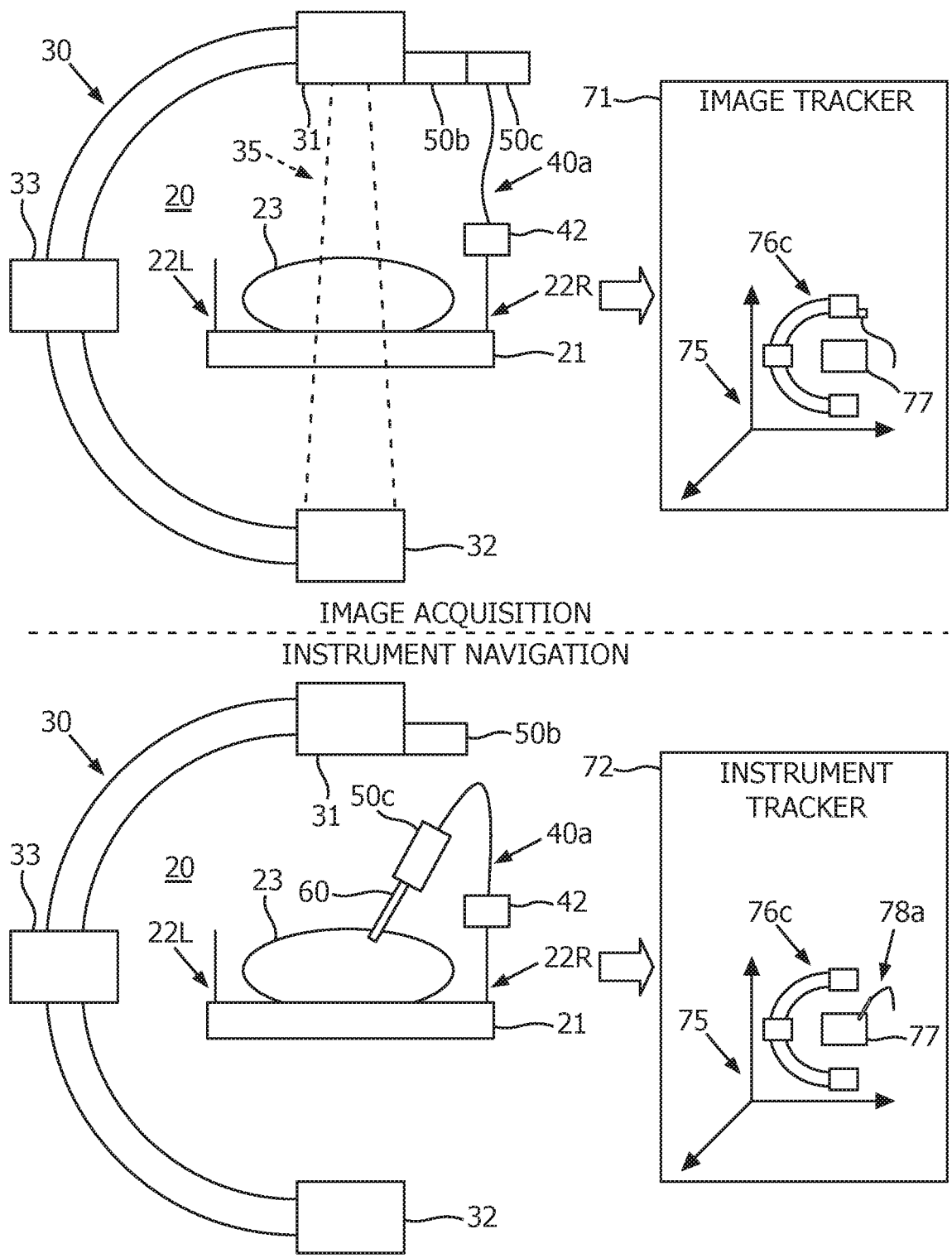
FIGS. 3A-3I illustrate nine (9) exemplary embodiments of the fluoroscopic surgical navigation of FIG. 1 employing a multi-piece mechanical connector having in accordance with the inventive principles of the present disclosure.

Referring to FIG. 3A, an image acquisition phase of the illustrated surgical procedure involves a detachable attachment of FORS sensor 40a to fluoroscopic imager 30 via an embedding of FORS sensor 40a into connector clip 50c. Prior to, concurrently or subsequently, the image acquisition phase further involves an emission of X-rays 35 by fluoroscopic imager 30. Image tracker 71 tracks a position and an orientation of resulting fluoroscopic image 77 within a coordinate system 75 of operating space 20 (e.g., a patient coordinate system) derived from a shape reconstruction 76c of FORS sensor 40a as attached to fluoroscopic imager 30.

A following instrument navigation phase of the surgical procedure involves a detachment of connector clip 50c from connector base 50b and a clipping, clamping or otherwise connection of connector base 50b into surgical instrument 60. Instrument tracker 72 tracks a position and an orientation of surgical instrument 60 within coordinate system 75 of operating space 20 derived from a shape reconstruction 78a of FORS sensor 40a as attached to surgical instrument 60.

Figure 3B:
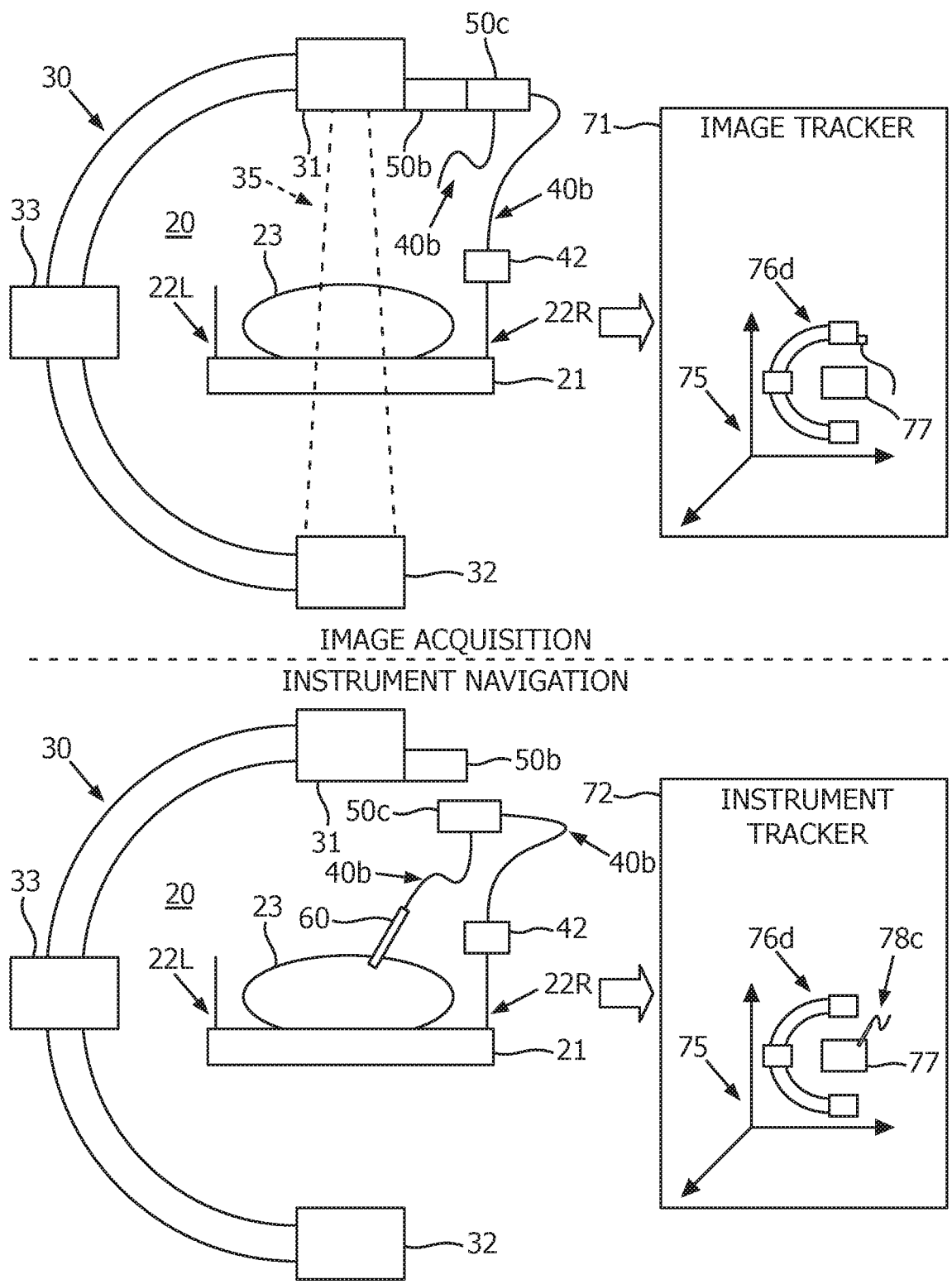

Referring to FIG. 3B, an image acquisition phase of the illustrated surgical procedure involves a detachable attachment of FORS sensor 40b to fluoroscopic imager 30 via an embedding of FORS sensor 40b through connector clip 50c. Prior to, concurrently or subsequently, the image acquisition phase further involves an emission of X-rays 35 by fluoroscopic imager 30. Image tracker 71 tracks a position and an orientation of resulting fluoroscopic image 77 within a coordinate system 75 of operating space 20 (e.g., a patient coordinate system) derived from a shape reconstruction 76d of FORS sensor 40b as attached to fluoroscopic imager 30.

As previously stated herein, FORS sensor 40b is a longer version of FORS sensor 40a (FIG. 3A). As such, the following instrument navigation phase of the surgical procedure involves a detachment of connector clip 50c from connector base 50b and an embedding of FORS sensor 40b into surgical instrument 60. Instrument tracker 72 tracks a position and an orientation of surgical instrument 60 within coordinate system 75 of operating space 20 derived from a shape reconstruction 78c of FORS sensor 40b as attached to surgical instrument 60.

Figure 3C:
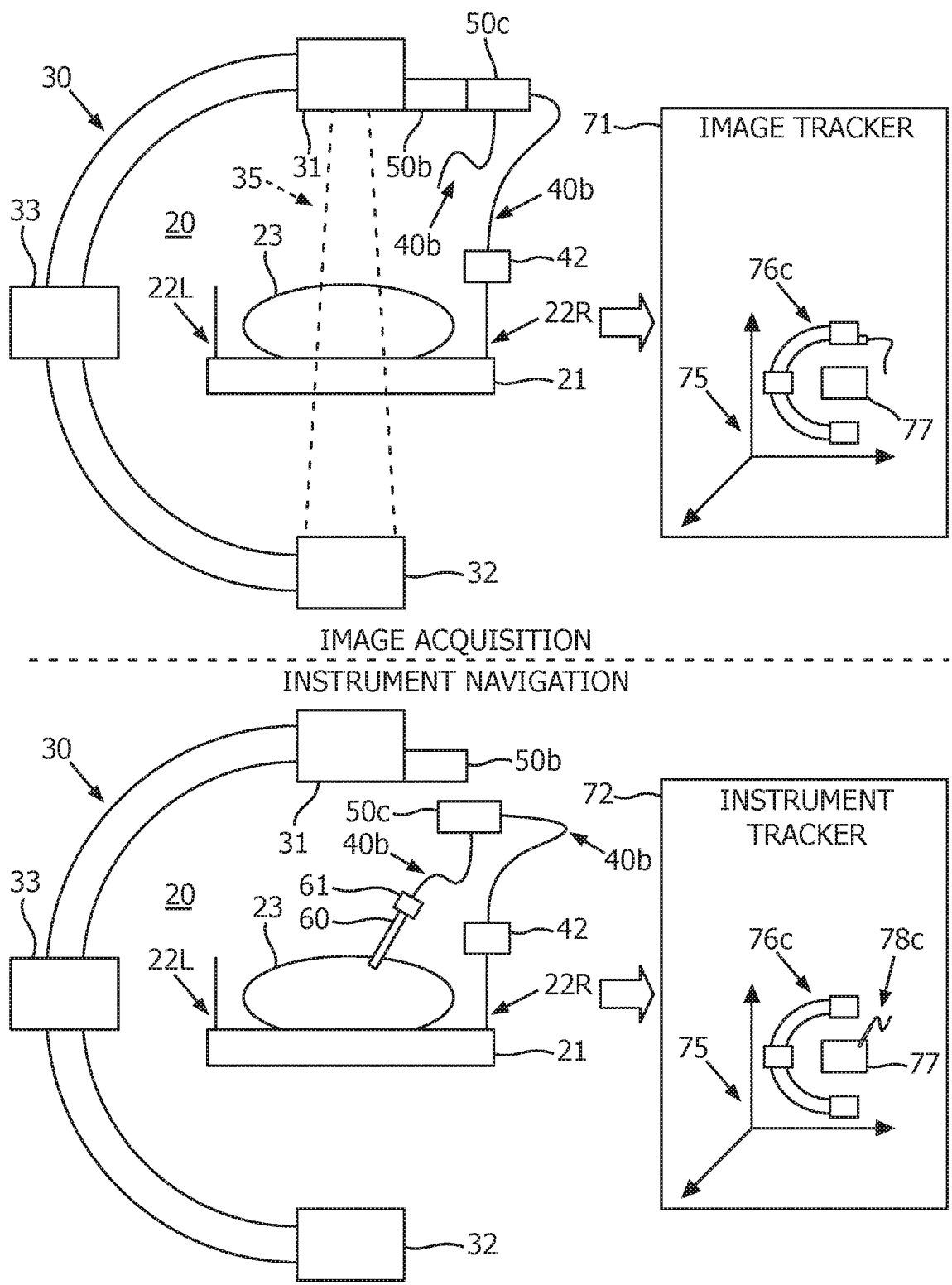

Referring to FIG. 3C, an image acquisition phase of the illustrated surgical procedure involves a detachable attachment of FORS sensor 40b to fluoroscopic imager 30 via an embedding of FORS sensor 40b through connector clip 50c. Prior to, concurrently or subsequently, the image acquisition phase further involves an emission of X-rays 35 by fluoroscopic imager 30. Image tracker 71 tracks a position and an orientation of resulting fluoroscopic image 77 within a coordinate system 75 of operating space 20 (e.g., a patient coordinate system) derived from a shape reconstruction 76c of FORS sensor 40b as attached to fluoroscopic imager 30.

The following instrument navigation phase of the surgical procedure involves a detachment of connector clip 50c from connector base 50b and an embedding of FORS sensor 40b into instrument connector 61, which is clipped, clamped or otherwise connected onto surgical instrument 60. Instrument tracker 72 tracks a position and an orientation of surgical instrument 60 within coordinate system 75 of operating space 20 derived from a shape reconstruction 78c of FORS sensor 40b as attached to surgical instrument 60.

Figure 3D:
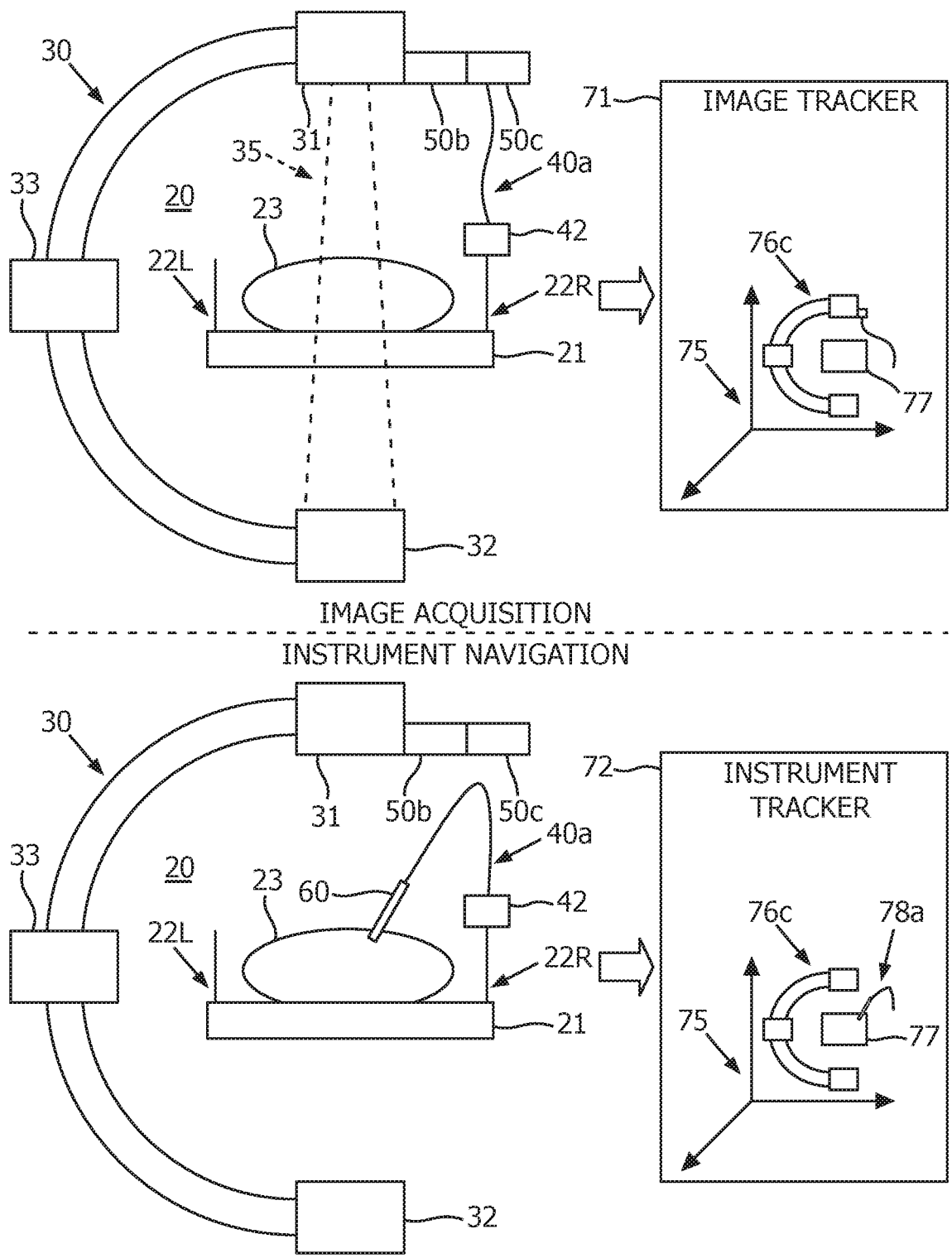

Referring to FIG. 3D, an image acquisition phase of the illustrated surgical procedure involves a detachable attachment of FORS sensor 40a to fluoroscopic imager 30 via an embedding of FORS sensor 40b into connector clip 50c. Prior to, concurrently or subsequently, the image acquisition phase further involves an emission of X-rays 35 by fluoroscopic imager 30. Image tracker 71 tracks a position and an orientation of resulting fluoroscopic image 77 within a coordinate system 75 of operating space 20 (e.g., a patient coordinate system) derived from a shape reconstruction 76c of FORS sensor 40a as attached to fluoroscopic imager 30.

A following instrument navigation phase of the surgical procedure involves a removal of FORS sensor 40a from connector clip 50c, and an embedding of FORS sensor 40a through surgical instrument 60. Instrument tracker 72 tracks a position and an orientation of surgical instrument 60 within coordinate system 75 of operating space 20 derived from a shape reconstruction 78a of FORS sensor 40a as attached to surgical instrument 60.

Figure 3E:
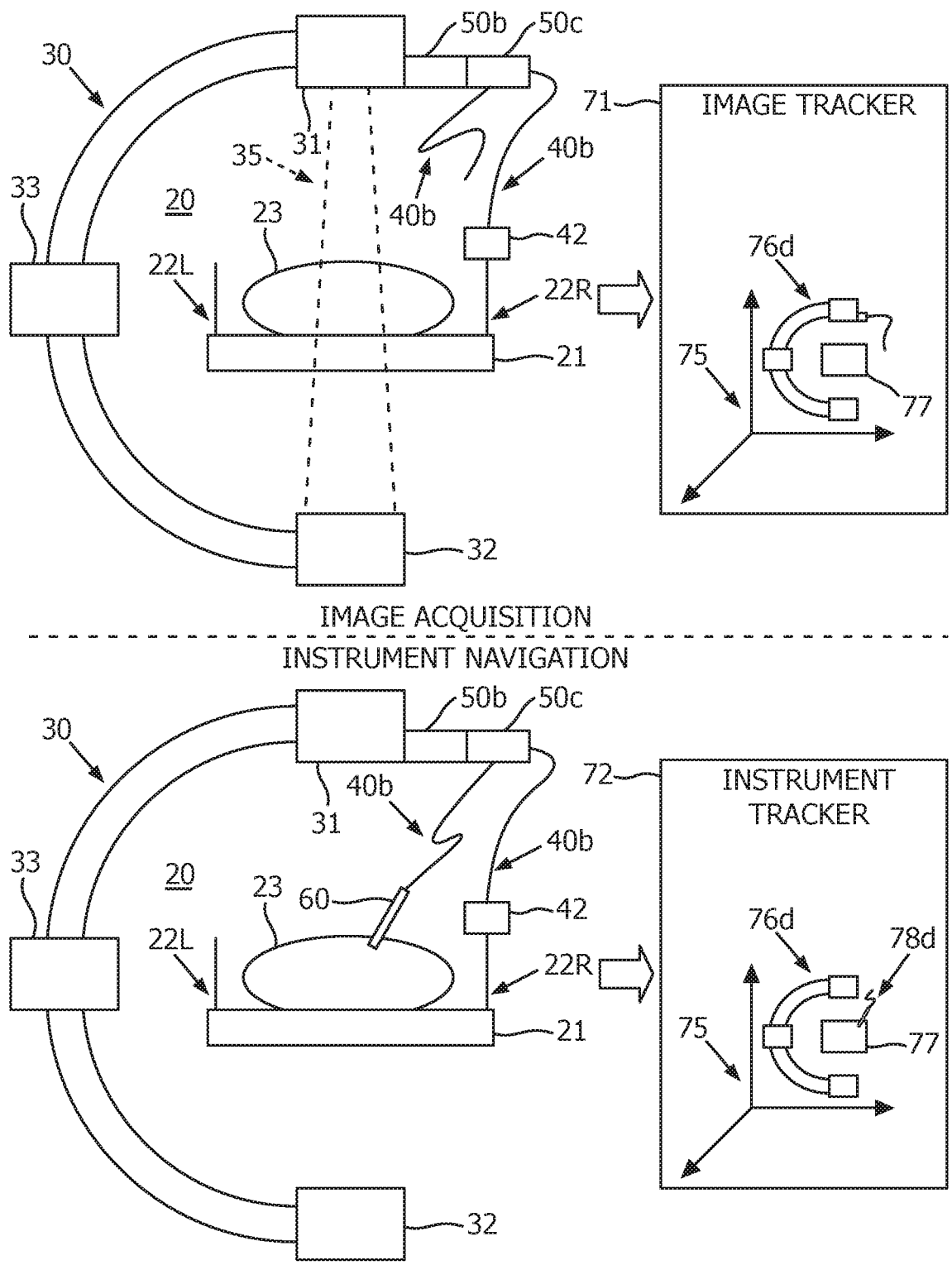

Referring to FIG. 3E, an image acquisition phase of the illustrated surgical procedure involves a detachable attachment of FORS sensor 40b to fluoroscopic imager 30 via an embedding of FORS sensor 40b through connector clip 50c. Prior to, concurrently or subsequently, the image acquisition phase further involves an emission of X-rays 35 by fluoroscopic imager 30. Image tracker 71 tracks a position and an orientation of resulting fluoroscopic image 77 within a coordinate system 75 of operating space 20 (e.g., a patient coordinate system) derived from a shape reconstruction 76d of FORS sensor 40b as attached to fluoroscopic imager 30.

The following instrument navigation phase of the surgical procedure involves FORS sensor 40b into surgical instrument 60 while maintaining the embedding of FORS sensor 40b through connector clip 50c. Instrument tracker 72 tracks a position and an orientation of surgical instrument 60 within coordinate system 75 of operating space 20 derived from a shape reconstruction 78d of FORS sensor 40b as attached to surgical instrument 60.

Figure 3F:
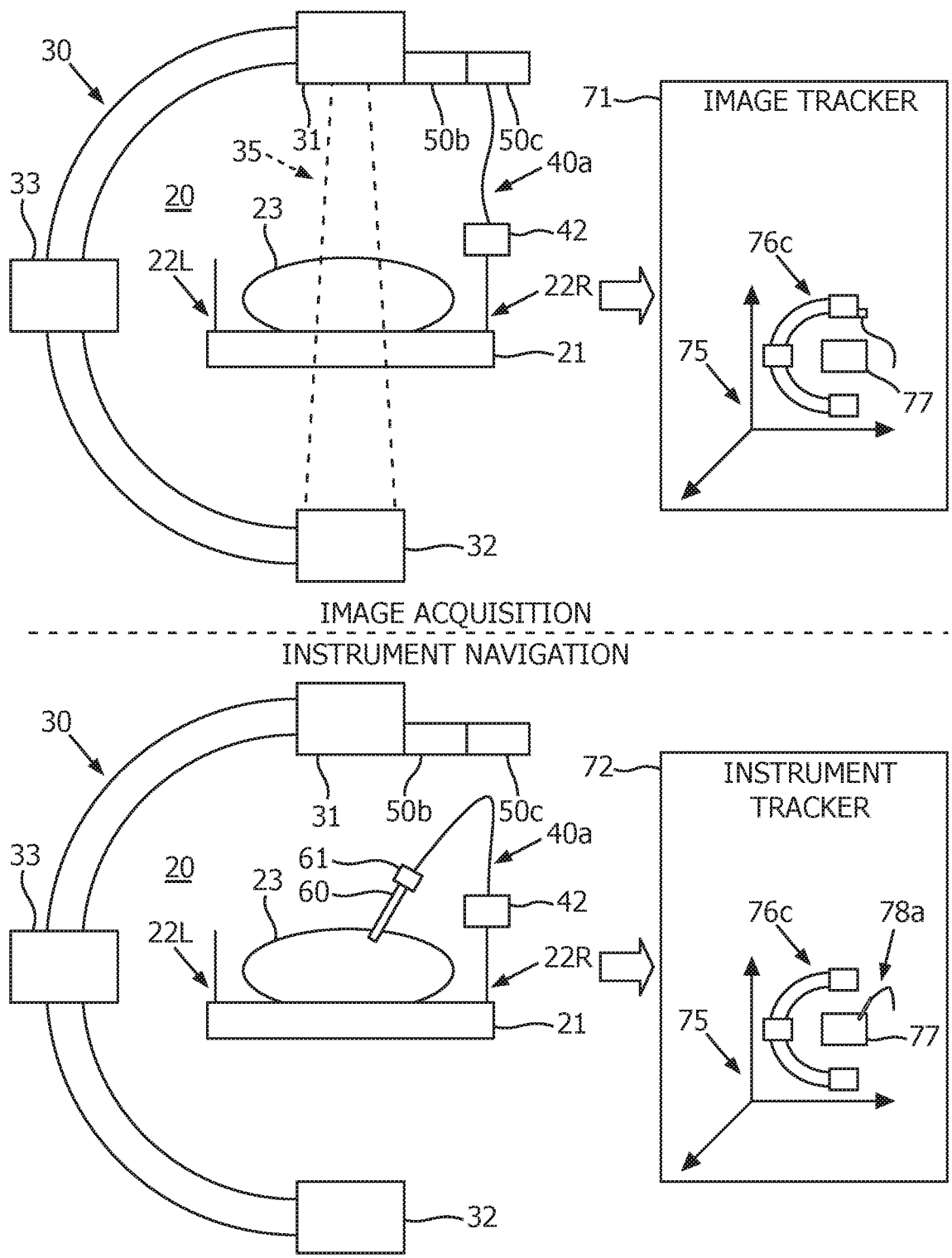

Referring to FIG. 3F, an image acquisition phase of the illustrated surgical procedure involves a detachable attachment of FORS sensor 40a to fluoroscopic imager 30 via an embedding of FORS sensor 40a into connector clip 50c. Prior to, concurrently or subsequently, the image acquisition phase further involves an emission of X-rays 35 by fluoroscopic imager 30. Image tracker 71 tracks a position and an orientation of resulting fluoroscopic image 77 within a coordinate system 75 of operating space 20 (e.g., a patient coordinate system) derived from a shape reconstruction 76c of FORS sensor 40a as attached to fluoroscopic imager 30.

The following instrument navigation phase of the surgical procedure involves a removal of FORS sensor 40a from connector clip 50c, and an embedding of FORS sensor 40a into instrument connector 61, which is clipped, clamped or otherwise connected onto surgical instrument 60. Instrument tracker 72 tracks a position and an orientation of surgical instrument 60 within coordinate system 75 of operating space 20 derived from a shape reconstruction 78a of FORS sensor 40a as attached to surgical instrument 60.

Figure 3G:
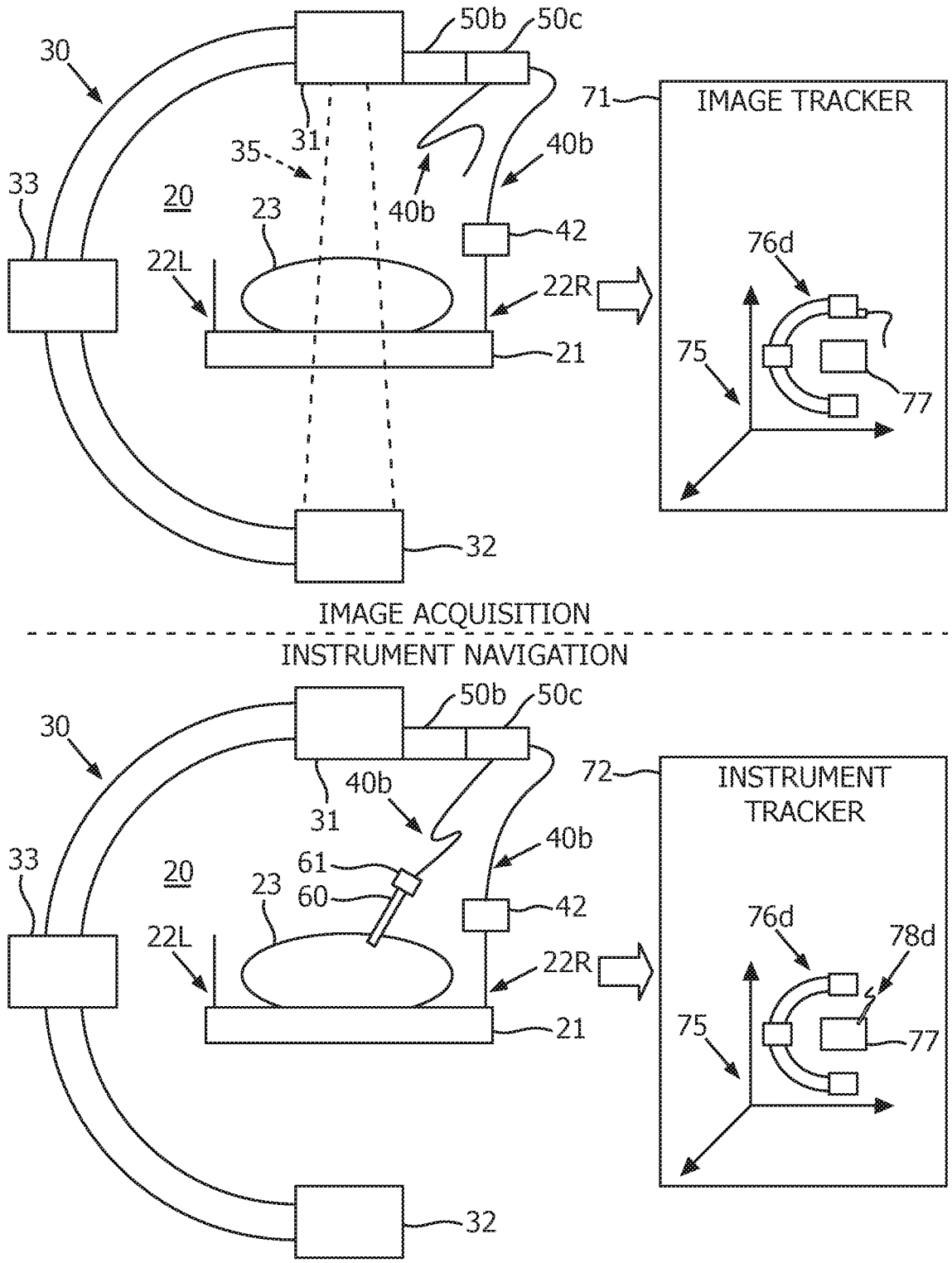

Referring to FIG. 3G, an image acquisition phase of the illustrated surgical procedure involves a detachable attachment of FORS sensor 40b to fluoroscopic imager 30 via an embedding of FORS sensor 40b through connector clip 50c. Prior to, concurrently or subsequently, the image acquisition phase further involves an emission of X-rays 35 by fluoroscopic imager 30. Image tracker 71 tracks a position and an orientation of resulting fluoroscopic image 77 within a coordinate system 75 of operating space 20 (e.g., a patient coordinate system) derived from a shape reconstruction 76d of FORS sensor 40b as attached to fluoroscopic imager 30.

The following instrument navigation phase of the surgical procedure involves an embedding of FORS sensor 40a into instrument connector 61, which is clipped, clamped or otherwise connected onto surgical instrument 60 while maintaining the embedding of FORS sensor 40b through connector clip 50c. Instrument tracker 72 tracks a position and an orientation of surgical instrument 60 within coordinate system 75 of operating space 20 derived from a shape reconstruction 78d of FORS sensor 40b as attached to surgical instrument 60.

Figure 3H:
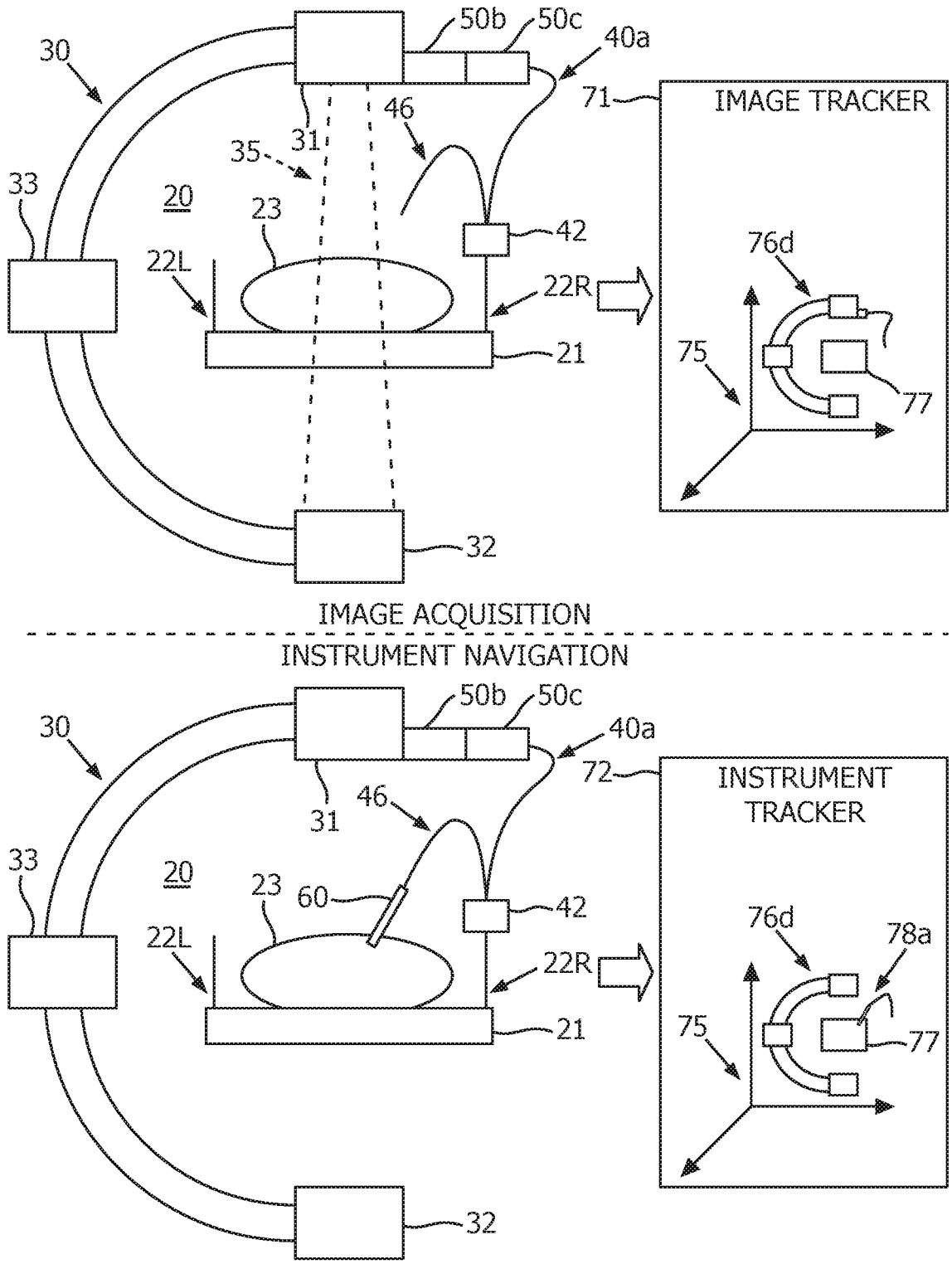

Referring to FIG. 3H, an image acquisition phase of the illustrated surgical procedure involves a detachable attachment of FORS sensor 40a to fluoroscopic imager 30 via an embedding of FORS sensor 40b into connector clip 50c. Prior to, concurrently or subsequently, the image acquisition phase further involves an emission of X-rays 35 by fluoroscopic imager 30. Image tracker 71 tracks a position and an orientation of resulting fluoroscopic image 77 within a coordinate system 75 of operating space 20 (e.g., a patient coordinate system) derived from a shape reconstruction 76d of FORS sensor 40a as attached to fluoroscopic imager 30.

A following instrument navigation phase of the surgical procedure involves an embedding of an auxiliary FORS sensor 46 into surgical instrument 60 while maintaining the embedding of FORS sensor 40a into connector clip 50c. Instrument tracker 72 tracks a position and an orientation of surgical instrument 60 within coordinate system 75 of operating space 20 derived from a shape reconstruction 78a of auxiliary FORS sensor 46 as attached to surgical instrument 60.

Figure 3I:
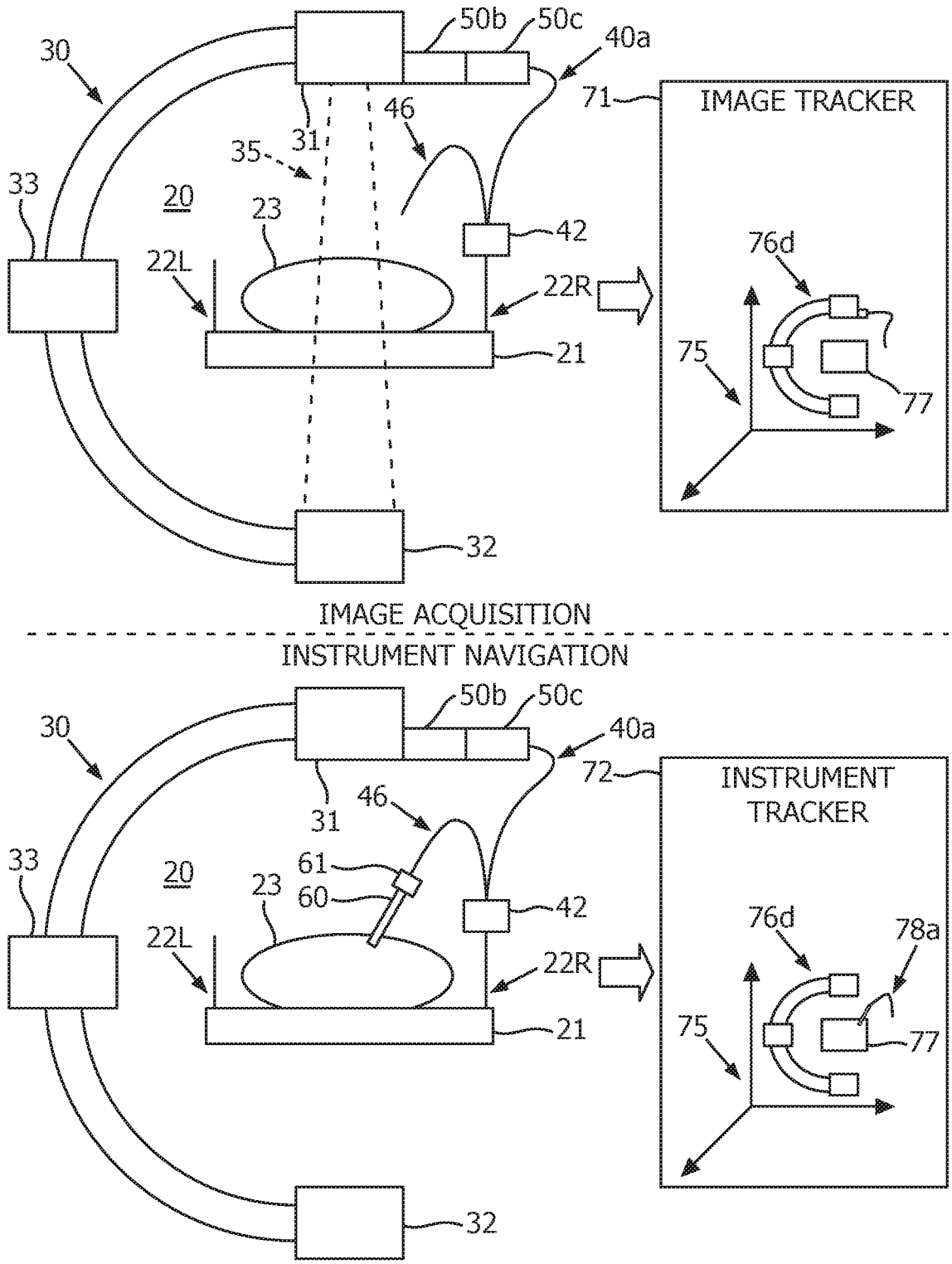

Referring to FIG. 3I, an image acquisition phase of the illustrated surgical procedure involves a detachable attachment of FORS sensor 40a to fluoroscopic imager 30 via an embedding of FORS sensor 40b into connector clip 50c. Prior to, concurrently or subsequently, the image acquisition phase further involves an emission of X-rays 35 by fluoroscopic imager 30. Image tracker 71 tracks a position and an orientation of resulting fluoroscopic image 77 within a coordinate system 75 of operating space 20 (e.g., a patient coordinate system) derived from a shape reconstruction 76a of FORS sensor 40a as attached to fluoroscopic imager 30.

A following instrument navigation phase of the surgical procedure involves an embedding of an auxiliary FORS sensor 46 into an instrument connector 61 clipped, clamped or otherwise connected onto surgical instrument 60 while maintaining the attachment of FORS sensor 40a to fluoroscopic imager 30 via connector clip 50c. Instrument tracker 72 tracks a position and an orientation of surgical instrument 60 within coordinate system 75 of operating space 20 derived from a shape reconstruction 78a of auxiliary FORS sensor 46 as attached to surgical instrument 60.

Referring back to FIG. 1, while fluoroscopic imager 30, FORS sensor 40 and mechanical connector 50 of the present disclosure is described as being particularly suitable for bi-plane imaging as shown with bi-plane images 84 and 85, in practice fluoroscopic imager 30, FORS sensor 40 and mechanical connector 50 are also suitable for single fluoroscopic imaging. To this end, launch 42 may still be utilized to establish a fixed reference point within operating space 20 as shown in FIG. 1, or alternatively, launch 42 may be omitted and optical fiber 41 may proximally extend from mechanical connector 50 (in the form of mechanical connector 50b or connector base 50b and connector clip 50c) to optical integrator 44 as shown in FIG. 4.

Figure 4:
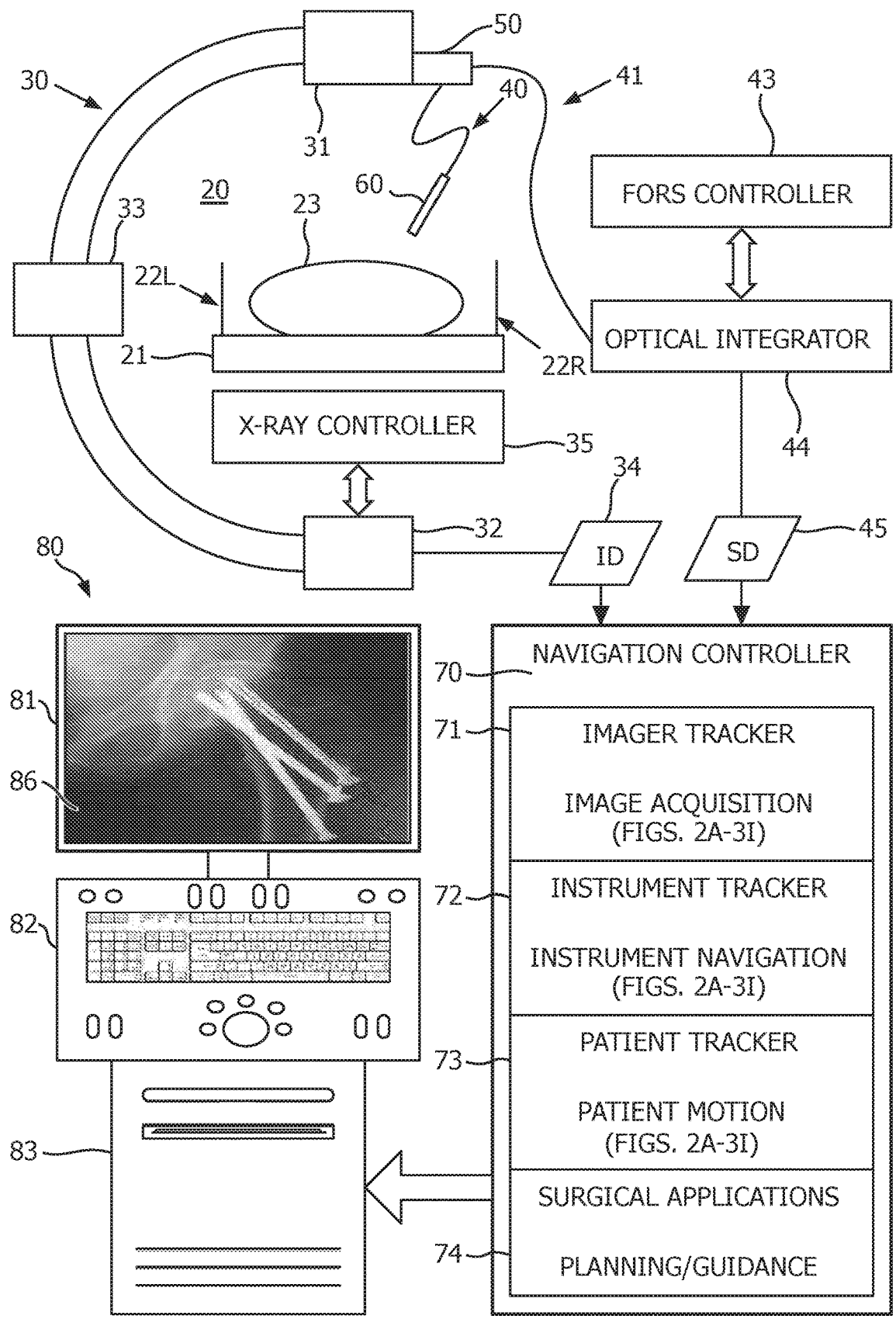
FIG. 4 illustrates an exemplary fluoroscopic surgical system, particularly for fluoroscopic imaging, in accordance with the inventive principles of the present invention.

Referring to FIG. 4, FORS sensor 40 distally extends from mechanical connector 50 whereby mechanical connector 50 serves as a reference point within operating space 20 that is movable in synchronization with any movement of fluoroscopic imager 30, or alternatively a reference point may be established at a fixed location of fluoroscopic imager 30 (e.g., a fixed location 47 as shown). Additionally, for tracking purposes of the spatial relationship between fluoroscopic imager 30 and surgical instrument 60, FORS sensor 40 is embedded into or otherwise attached to surgical instrument 60 or an instrument connector (not shown) in accordance with the inventive principles of the present disclosure as previously described herein. The tracking of the spatial relationship between fluoroscopic imager 30 and surgical instrument 60 facilitates a display by the image guidance application of an overlay of surgical instrument 60 onto the fluoroscopic image (e.g., fluoroscopic image 86 as shown displayed by monitor 81).

Referring to FIGS. 1 and 4, to further facilitate an understanding of the various inventions of the present disclosure, the following description of FIGS. 5A, 5B, 6A and 6B teaches basic inventive principles of an implementation of a FORS sensing by a fluoroscopic surgical system during a surgical procedure incorporating an embedding of FORS sensor 40 into or through mechanical connector 50a, connector clip 50c and surgical instrument 60 as well as an instrument connector 61 (FIG. 2C). From this description, those having ordinary skill in the art will appreciate how to apply the inventive principles of the present disclosure for making and using additional embodiment of fluoroscopic surgical systems and methods of the present disclosure incorporating such embedding of FORS sensor 40. Please note the components of the present disclosure as shown in FIGS. 5A, 5B, 6A and 6B are not drawn to scale, but drawn to conceptually visualize the inventive principles of the present disclosure.

Figure 5A:
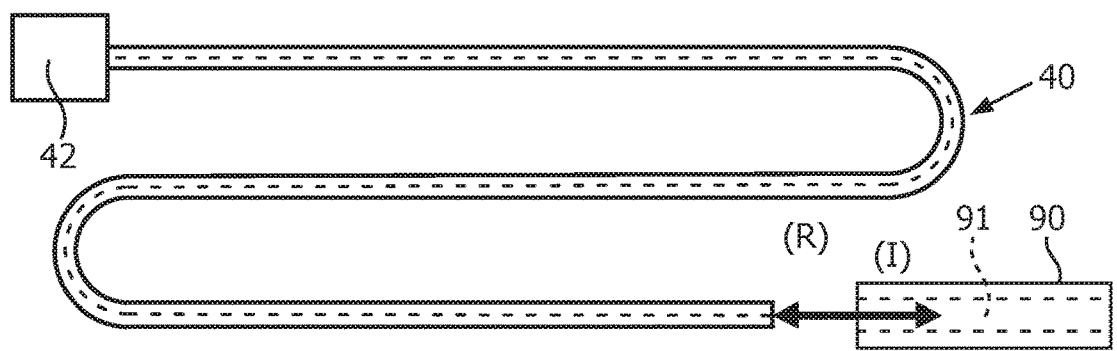
FIGS. 5A and 5B illustrate an exemplary embodiment of a FORS sensor in accordance with the inventive principles of the present disclosure.

Referring to FIG. 5A, FORS sensor 40 distally extends from launch 42 and has a diameter sized to be insertable (I) into and retractable (R) from within a lumen 91 of an object 90, which is representative of mechanical connector 50a (FIG. 1), surgical instrument 60 (FIG. 1) and instrument connector 61 (FIG. 2C). In practice, upon insertion into lumen 91 of objet 90, FORS sensor 40 may partially or entirely occupy lumen 91 of object 90, or extend through and out of lumen 91 of object 90 depending on the intended tracking use of FOR sensor 40.

Figure 5B:
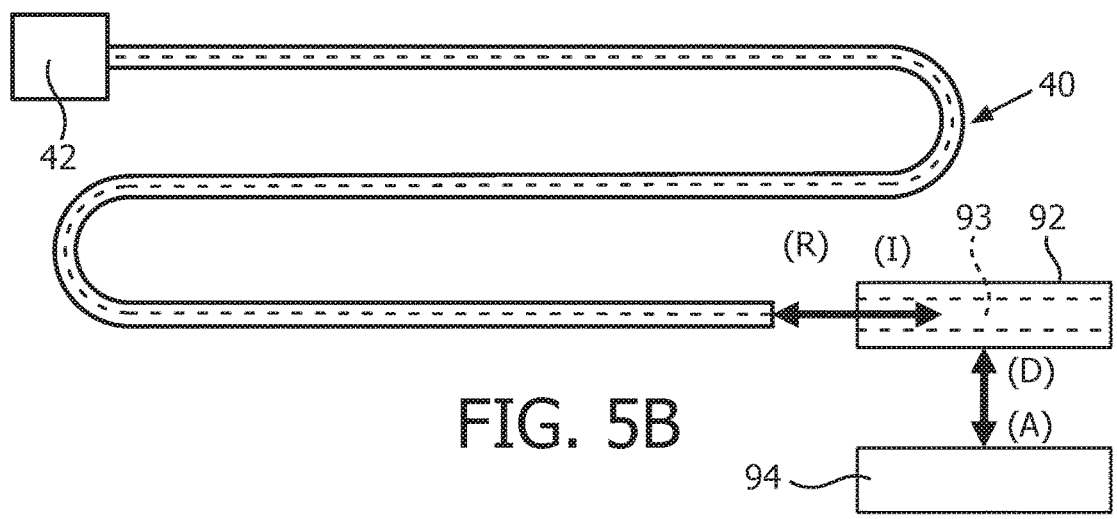

Referring to FIG. 5B, FORS sensor 40 distally extends from launch 42 and has a diameter sized to be insertable (I) into and retractable (R) from within a lumen 93 of an object 92, which is representative of connector clip 50c (FIG. 1). Object 92 is attachable (A) to and detachable (D) from an object 94, which is representative of connector base 50b (FIG. 1) and surgical instrument 60 (FIG. 1). In practice, upon insertion into lumen 93 of objet 92, FORS sensor 40 may partially or entirely occupy lumen 93 of object 92, or extend through and out of lumen 93 of object 92 depending on the intended tracking use of FOR sensor 40.

Figures 6A, 6B:
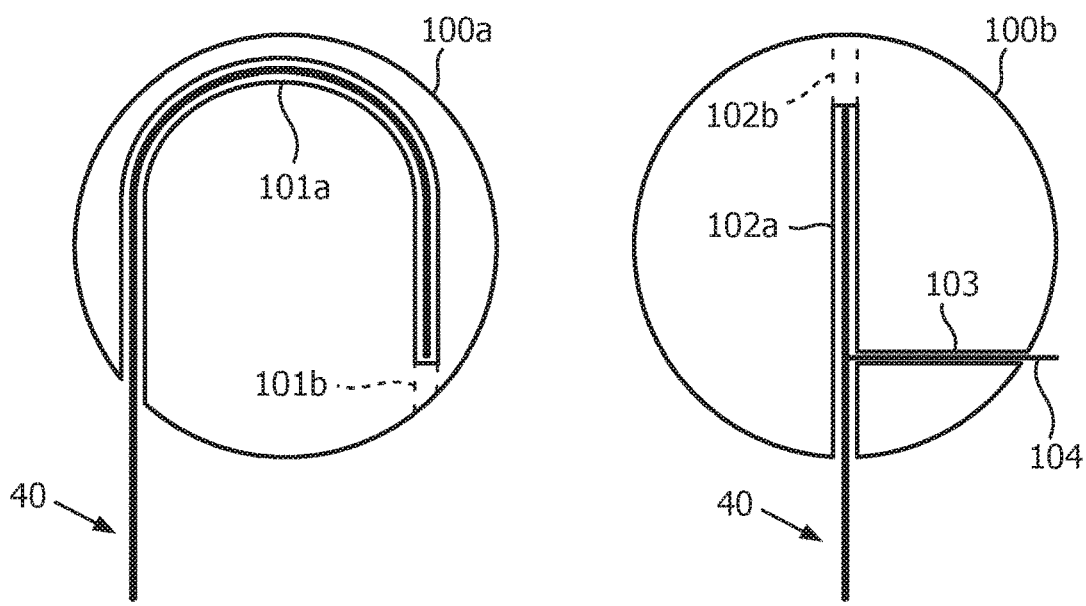
FIGS. 6A and 6B illustrate two (2) exemplary embodiments of a connector clip in accordance with the inventive principles of the present disclosure.

Referring to FIG. 6A, mechanical connector 50a (FIG. 1) or connector clip 50c (FIG. 1) may be embodied as a clip 100a having a lumen 101a of a semi-oval shape for a friction fitted insertion and retraction of FORS sensor 40 into clip 100a, or alternatively for a permanent embedding of FORS sensor 40 within clip 100a. Lumen 101a may have an extension 101b for a friction fitted insertion and retraction of FORS sensor 40 through clip 100a. In practice, FORS sensor 40 may Referring to FIG. 6B, mechanical connector 50a (FIG. 1) or connector clip 50c (FIG. 1) may be embodied as a clip 100b having a lumen 102a for insertion and retraction of FORS sensor into clip 100b and a screw 104 extending through a channel 102 intersecting lumen 102a for temporarily or permanently securing FOR sensor 40 within lumen 102a. Lumen 102a may have an extension 102b for a friction fitted insertion and retraction of FORS sensor 40 through clip 100b.

Referring back to FIGS. 1 and 4, in practice, the fluoroscopic surgical system of the present disclosure will typically be draped with sterile drapes whereby attachment methodology of the present disclosure must be able to account for the presence of the drape and yet facilitate repeatable attachment of FORS sensor 40 to fluoroscopic imager 30. FIGS. 7A-7D illustrate exemplary embodiments of the present disclosure addressing the incorporation of drapes.

Figure 7A:
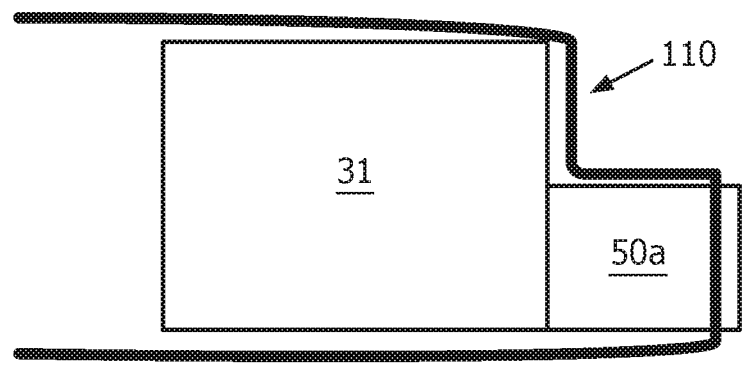
FIGS. 7A-7D illustrate four (4) exemplary embodiments of a drape integration with a mechanical connector in accordance with the inventive principles of the present disclosure.

Referring to FIG. 7A, a sterile drape 110 may be integrated with mechanical connector 50*a* as shown. For this embodiment, mechanical connector 50*a* must be sterile or sterilized between surgical procedures.

Figure 7B:
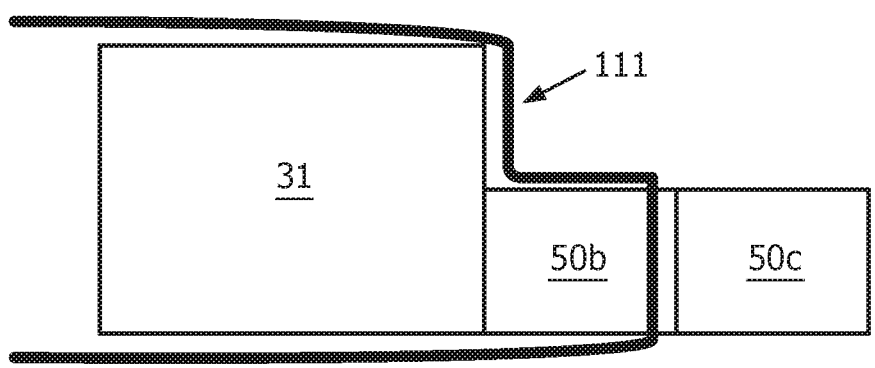

Referring to FIG. 7B, sterile drape 110 may be integrated with connector base 50*b* as shown. For this embodiment, connector base 50*b* and connector clip 50*c* must be sterile or sterilized between surgical procedures.

Figure 7C:
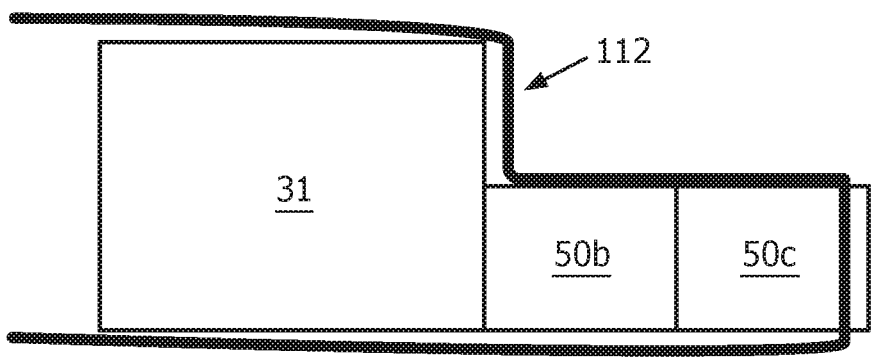

Referring to FIG. 7C, sterile drape 110 may be integrated with connector clip 50*c* as shown. For this embodiment, connector clip 50*c* must be sterile or sterilized between surgical procedures.

Figure 7D:
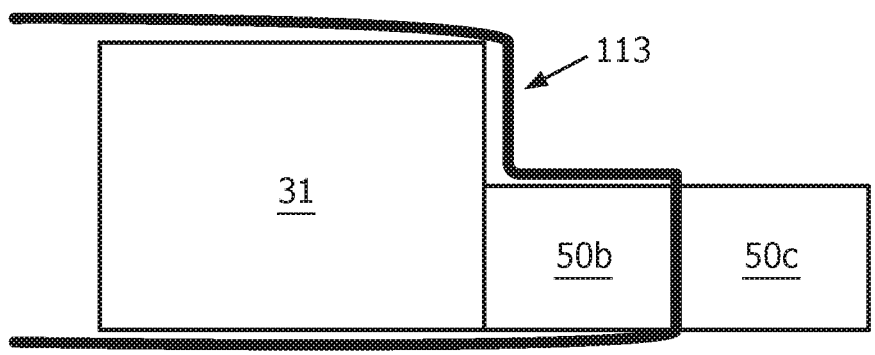

Referring to FIG. 7D, sterile drape 110 is disposed between connector base 50*b* and connector clip 50*c* as shown whereby sterile drape 110 may or may not be punctured by an attachment of connector clip 50*c* to connector base 50*b*. For this embodiment, connector clip 50*c* must be sterile or sterilized between surgical procedures.

An exemplary workflow of the fluoroscopic surgical system including a registration phase, a calibration phase and a tracking phase will now be described herein in the context of FIG. 3A. From this description, those having ordinary skilled in the art will know how to apply the inventive principles of the present disclosure to additional workflow embodiments. More particularly, in practice, a workflow embodiment of the present disclosure may not require a registration phase and a calibration phase for all components. For example, one advantage of the various inventions of the present disclosure is fluoroscopic imager 30 and FORS sensor 40 are automatically registered to each other through use of launch 42 or any other fixed reference position within operating space 20. Additionally, in practice, a calibration between fluoroscopic imager 30 and mechanical connector 50 will typically not be required, and if more than FORS sensor is employed, then the FORS sensors may be registered to each other in one of many registration techniques as known in the art.

Registration Phase (FORS sensor 40). A user of the system sets up the fluoroscopy surgical system via a coupling of FORS sensor 40 to optical integrator 44 as known in the art, and attaches launch 42 to rail 22R of operating table 21. The user may subsequently activate a registration module (not shown) of navigation controller 80 via keyboard 82 as needed to register a launch position of FORS sensor 40, or another registration position of FORS sensor 40 distally spaced from launch 42 to a pre-operative image of patient anatomy 23. In practice, any known applicable registration technique may be executed by the registration module.

Calibration Phase (FORS sensor 40/mechanical connector 50). The user of the fluoroscopic surgical system securely attaches FORS sensor 40 to fluoroscopic imager 30 via an insertion of FORS sensor 40 into or through connector clip 50*c* as previously described herein. The user subsequently activates a calibration module (not shown) of navigation controller 70 via keyboard 82 as needed to calibrate FORS sensor 40 to fluoroscopic imager 30.

More particularly, the calibration is premised on a rigid relationship between FORs sensor 40 and connector clip 50*c*. As such, in practice, any known applicable calibration technique may be executed for calibrating FORS sensor 40 and fluoroscopic imager 30.

Alternative to known calibration techniques, the present disclosure provides a calibration technique involving an automatic detection and calibration of connector clip 50*c* through a lumen shape that is unique to connector clip 50*c* of the present disclosure. Specifically, once FORS sensor 40 is inserted into or through the lumen of connector clip 50*c*, the calibration module of navigation controller 70 automatically detects fluoroscopic imager 30 based on one or more of shape parameters (curvature, position, orientation, axial strain, etc.) of a shape reconstruction of FORS sensor 40.

Tracking Phase (fluoroscopic imager 30). Upon completion of registration of FORS sensor 40 and calibration of FORS sensor 40 to fluoroscopic imager 30, imager tracker 71 controls a tracking of a position and orientation of fluoroscopic imager 33 within operating space 20 derived from a shape reconstruction of FORS sensor 40 as known in the art. In practice, the tracking phase for fluoroscopic imager 30 may be implemented each time fluoroscopic imager 30 is rotated relative to patient anatomy 23.

Calibration Phase (FORS sensor 40/surgical instrument 60). The user of the fluoroscopic surgical system detaches connector clip 50*c* from connector base 50*b*, and attaches connector clip 50*c* to surgical instrument 60. The user subsequently activates calibration module 112 via keyboard 112 as needed to calibrate FORS sensor 40 to surgical instrument 60. The user subsequently activates the calibration module (not shown) of navigation controller 70 via keyboard 82 as needed to calibrate FORS sensor 40 to surgical instrument 60. More particularly, the calibration is premised on a rigid relationship between FORs sensor 40 and surgical instrument 60. As such, in practice, any known applicable calibration technique may be executed for calibrating FORS sensor 40 and fluoroscopic imager 30.

Tracking Phase (surgical instrument 60). Upon completion of registration of FORS sensor 40 and calibration of FORS sensor 40 to surgical instrument 60, instrument tracker 71 controls a tracking of a position and orientation of surgical instrument 60 within operating space 20 derived from a shape reconstruction of FORS sensor 40 as known in the art.

In practice, image guidance may be implemented whereby surgical instrument 60 may be selected from a database, and then a model of surgical instrument 60 may be displayed based on the shape sensing position and orientation of FORS sensor 40.

Also in practice, a tracking accuracy for imaging guidance may be refined as desired.

For example, an image-based refinement may involve the user of the system identifying a tip of surgical instrument 60 in the image overlay whereby a distance between the distal ends of FORS sensor 40 and surgical instrument 60 is measured and then used to extrapolate the shape of FORS sensor 40 by the appropriate amount. If there is significant error that is not in the longitudinal direction of surgical instrument 60, then this error is detected and identified to the user.

By further example, in pre-calibration, the user may place connector clip 50*c* into a specific position on launch 60 (or another known position), and a distance between the known position and the measured position of the distal end of FORS sensor 40 is computed. If there is significant error that is not in the longitudinal direction of the distal end of FORS sensor 40, then this error is detected and identified to the user.

By further example, an execution of a known technique for determining longitudinal offset between a tip of FORS sensor 40 and measurement of the tip of the FORS sensor 40 is implemented by the user through a pivot fixture.

Referring to FIGS. 1-7, those having ordinary skill in the art will appreciate numerous benefits of the present invention including, but not limited to, overcoming a number of challenges specific to the integration of FORS sensing into a typical orthopedic workflow with a mobile c-arm. In particular, the solution of the present disclosure proposes a preferable use of a single FORS sensor, which is beneficial for several reasons:

First, using multiple active FORS sensors adds additional cost. While the present disclosure is applicable to multiple active FORS sensors, the solution of the present disclosure allows for only a single FORS sensor to be used during the procedure.

Second, a single FORS sensor reduces complexity, improves workflow, and decreases clutter in the workspace.

Third, because the single FORS sensor is fixed to a stationary position in the room, it provides a seamless registration between the imaging and navigation.

Finally, the workflow of the procedure often involves the c-arm being moved away from the patient to provide better access. The solution of the present disclosure facilitates this workflow.

Further, as one having ordinary skill in the art will appreciate in view of the teachings provided herein, features, elements, components, etc. described in the present disclosure/specification and/or depicted in the Figures may be implemented in various combinations of hardware and software, and provide functions which may be combined in a single element or multiple elements. For example, the functions of the various features, elements, components, etc. shown/illustrated/depicted in the Figures can be provided through the use of dedicated hardware as well as hardware capable of executing software in association with appropriate software for added functionality. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Having described preferred and exemplary embodiments of novel and inventive Fiber Optical RealShape sensing for fluoroscopic based surgical procedure, (which embodiments are intended to be illustrative and not limiting), it is noted that modifications and variations can be made by persons skilled in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device/system or such as may be used/implemented in/with a device in accordance with the present disclosure are also contemplated and considered to be within the scope of the present invention. Further, corresponding and/or related method for manufacturing and/or using a device and/or system in accordance with the present disclosure are also contemplated and considered to be within the scope of the present invention.

The invention claimed is:

1. A fluoroscopic surgical system, comprising:
   an optical shape sensor configured to generate sensing data informative of a shape reconstruction of the optical shape sensor relative to a reference position within an operating space;
   a fluoroscopic imager;
   a mechanical connector adjoined to the fluoroscopic imager, wherein the mechanical connector is configured to detachably attach the optical shape sensor to the fluoroscopic imager such that the shape reconstruction of the optical shape sensor indicates a position and orientation of the fluoroscopic imager; and
   a navigation controller configured to control a tracking of the fluoroscopic imager within the operating space responsive to the sensing data by the optical shape sensor based on a detachable attachment of the optical shape sensor by the mechanical connector.

2. The fluoroscopic surgical system of claim 1, wherein the attachment of the optical shape sensor to the fluoroscopic imager includes the optical shape sensor being embedded within the mechanical connector.

3. The fluoroscopic surgical system of claim 1, further comprising:
   a drape integrated with the mechanical connector.

4. The fluoroscopic surgical system of claim 1, wherein the mechanical connector includes:
   a connector base adjoined to the fluoroscopic imager; and
   a connector clip configured to detachably attach the optical shape sensor to the connector base.

5. The fluoroscopic surgical system of claim 4, wherein the attachment of the optical shape sensor to the connector base by the connector clip includes the optical shape sensor being embedded within the connector clip.

6. The fluoroscopic surgical system of claim 4, further comprising:
   a drape,
      wherein the attachment of the optical shape sensor to the connector base by the connector clip includes the drape being disposed between the connector base and the connector clip.

7. The fluoroscopic surgical system of claim 4, further comprising:
a drape integrated with at least one of the connector base and the connector clip.

8. The fluoroscopic surgical system of claim 4, further comprising:
a surgical instrument,
wherein the connector clip is further structurally configured to detachably attach the optical shape sensor to the surgical instrument, and
wherein the navigation controller is further structurally configured to control a tracking of the surgical instrument within the operating space responsive to a generation of the sensing data by the optical shape sensor based on a detachable attachment of the optical shape sensor to the surgical instrument by the connector clip.

9. The fluoroscopic surgical system of claim 4, further comprising:
a surgical instrument; and
an auxiliary optical shape sensor structurally configured to generate auxiliary sensing data informative of a shape reconstruction of the auxiliary optical shape sensor relative to the reference position within the operating space,
wherein the a connector clip is further structurally configured to detachably attach the auxiliary optical shape sensor to the surgical instrument, and
wherein the navigation controller is further structurally configured to control a tracking of the surgical instrument within the operating space responsive to a generation of the auxiliary sensing data by the auxiliary optical shape sensor based on a detachable attachment of the auxiliary optical shape sensor to surgical instrument by the a connector clip.

10. The fluoroscopic surgical system of claim 1, further comprising:
a surgical instrument,
wherein the optical shape sensor is further configured to be embedded within the surgical instrument such that the sensing data generated by the optical shape sensor further indicates a position and orientation of the surgical instrument, and
wherein the navigation controller is further configured to control a tracking of the surgical instrument within the operating space responsive to the sensing data by the optical shape sensor based on an embedding of the optical shape sensor within the surgical instrument.

11. The fluoroscopic surgical system of claim 1, further comprising:
a surgical instrument; and
an instrument connector structurally configured to detachably attach the optical shape sensor to the surgical instrument, and
wherein the navigation controller is further structurally configured to control a tracking of the surgical instrument within the operating space responsive to a generation of the sensing data by the optical shape sensor based on a detachable attachment of the optical shape sensor to the surgical instrument by the instrument connector.

12. The fluoroscopic surgical system of claim 1, further comprising:
a surgical instrument; and
an auxiliary optical shape sensor structurally configured to generate auxiliary sensing data informative of a shape reconstruction of the auxiliary optical shape sensor relative to the reference position within the operating space,
wherein the auxiliary optical shape sensor is structurally configured to be embedded within the surgical instrument, and
wherein the navigation controller is further structurally configured to control a tracking of the surgical instrument within the operating space responsive to a generation of the auxiliary sensing data by the auxiliary optical shape sensor based on an embedding of the auxiliary optical shape sensor within the surgical instrument.

13. The fluoroscopic surgical system of claim 1, further comprising:
a surgical instrument;
an auxiliary optical shape sensor structurally configured to generate auxiliary sensing data informative of a shape reconstruction of the auxiliary optical shape sensor relative to the reference position within the operating space; and
an instrument connector structurally configured to detachably attach the auxiliary optical shape sensor to the surgical instrument,
wherein the navigation controller is further structurally configured to control a tracking of the surgical instrument within the operating space responsive to a generation of the auxiliary sensing data by the auxiliary optical shape sensor based on a detachable attachment of the auxiliary optical shape sensor to surgical instrument by the instrument connector.

14. The fluoroscopic surgical system of claim 1, further comprising:
a launch,
wherein the optical shape sensor distally extends from launch, and
wherein the reference position is fixed within the operating space.

15. The fluoroscopic surgical system of claim 1, wherein the reference position is movable within the operating space based on the detachable attachment of the optical shape sensor to the fluoroscopic imager.

16. A fluoroscopic surgical method, comprising:
detachably attaching an optical shape sensor to a fluoroscopic imager;
based on the detachable attachment of the optical shape sensor to the fluoroscopic imager, generating sensing data informative of a shape reconstruction of the optical shape sensor relative to a reference position within an operating space, the shape reconstruction being indicative of a position and orientation of the fluoroscopic imager;
controlling a tracking of the fluoroscopic imager within the operating space responsive to the sensing data generated by the optical shape sensor based on the detachable attachment of the optical shape sensor to the fluoroscopic imager;
detaching the optical shape sensor from the fluoroscopic imager and detachably attaching the optical shape sensor to a surgical instrument, or concurrently detachably attaching the optical shape sensor to the fluoroscopic imager and the surgical instrument;
based on the detachable attachment of the optical shape sensor to the surgical instrument, generating sensing data informative of the shape reconstruction of the optical shape sensor relative to the reference position within the operating space; and controlling a tracking of the surgical instrument within the operating space responsive to the sensing data generated by the optical shape sensor based on the detachable attachment of the optical shape sensor to the surgical instrument.

17. The fluoroscopic method of claim 16, further comprising:

generating imaging data illustrative of a fluoroscopic image; and controlling a visual representation of the surgical instrument within at least one of the fluoroscopic image and an operative image, wherein the visual representation of the surgical instrument is derived by a navigation controller from the tracking of the fluoroscopic imager and the surgical instrument within the operating space.

18. The fluoroscopic method of claim 17, wherein the fluoroscopic imager generates the imaging data concurrent to or subsequent to the detachable attachment of the optical shape sensor to the fluoroscopic imager.

19. A fluoroscopic surgical system, comprising:

an optical shape sensor detachably attached to a fluoroscopic imager, and configured to generate sensing data informative of a shape reconstruction of the optical shape sensor relative to a reference position within an operating space, the shape reconstruction of the optical shape sensor indicating a position and orientation of the fluoroscopic imager to which the optical shape sensor is detachably attached; and a navigation controller configured to control a tracking of the fluoroscopic imager within the operating space responsive to the sensing data generated by the optical shape sensor based on the detachable attachment of the optical shape sensor to the fluoroscopic imager;

wherein the optical shape sensor is configured to serve as a surgical instrument;

wherein the optical shape sensor, based on the optical shape sensor serving as the surgical instrument, further generates sensing data informative of the shape reconstruction of the optical shape sensor relative to the reference position within the operating space; and wherein the navigation controller further controls a tracking of the optical shape sensor within the operating space responsive to the sensing data generated by the optical shape sensor based on the optical shape sensor serving as the surgical instrument.

20. The fluoroscopic system of claim 19, wherein:

the fluoroscopic imager generates imaging data illustrative of a fluoroscopic image;

the navigation controller further controls a visual representation of the surgical instrument within at least one of the fluoroscopic image and an operative image; and the visual representation of the surgical instrument is derived by the navigation controller from the tracking of the fluoroscopic imager and the surgical instrument within the operating space.

* * * * *